United States Patent
Greenberg et al.

(10) Patent No.: US 9,029,346 B1
(45) Date of Patent: May 12, 2015

(54) IRREVERSIBLE INHIBITORS OF DNA POLYMERASE BETA

(71) Applicant: The Johns Hopkins University, Baltimore, MD (US)

(72) Inventors: Marc M. Greenberg, Baltimore, MD (US); Dumitru Arian, Chisinau (MD); Theodore L. Deweese, Towson, MD (US); Mohammad Hedayati, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/106,016

(22) Filed: Dec. 13, 2013

(51) Int. Cl.
  *A01N 43/04* (2006.01)
  *A61K 31/70* (2006.01)
  *C07H 19/10* (2006.01)

(52) U.S. Cl.
  CPC .................................... *C07H 19/10* (2013.01)

(58) Field of Classification Search
  None
  See application file for complete search history.

(56) References Cited

U.S. PATENT DOCUMENTS 7,544,794 B1 * 6/2009 Benner ...................... 536/27.61

\* cited by examiner

*Primary Examiner* — Patrick Lewis
(74) *Attorney, Agent, or Firm* — Ward and Smith, P.A.

(57) ABSTRACT

Methods and compounds are disclosed for irreversibly inhibiting a DNA repair enzyme that possesses lyase activity.

21 Claims, 14 Drawing Sheets

IRREVERSIBLE INHIBITORS OF DNA POLYMERASE BETA

FEDERALLY SPONSORED RESEARCH OR DEVELOPMENT

This invention was made with government support under GM-063028 awarded by the National Institutes of Health (NIH). The government has certain rights in the invention.

BACKGROUND

Base excision repair (BER) is a primary mechanism for maintaining genome integrity. A large variety of modified nucleotides resulting from DNA oxidation and alkylation are removed by glycosylases (Friedberg et al., 2006). Abasic (AP) sites are ubiquitous DNA lesions that are mutagenic and cytotoxic. Some BER glycosylases are bifunctional and cleave DNA at a transiently formed AP site via a lyase process (Stivers et al, 2003). In other instances, AP sites are produced as metastable intermediates. AP sites also are generated via spontaneous hydrolysis of native and damaged nucleotides. DNA polymerase β (Pol β), a bifunctional enzyme that contains an 8 kDa lyase active site separate from its polymerase active site (Matsumoto and Kim, 1995; Matsumoto et al., 1998; Prasad et al., 1998), plays an integral role in BER by excising the remnant of an AP site following 5'-incision by apurinic endonuclease 1 (Ape1), and subsequently filling in the single nucleotide gap (Scheme 1).

Scheme 1. Role of DNA polymerase β (Pol β) in base excision repair

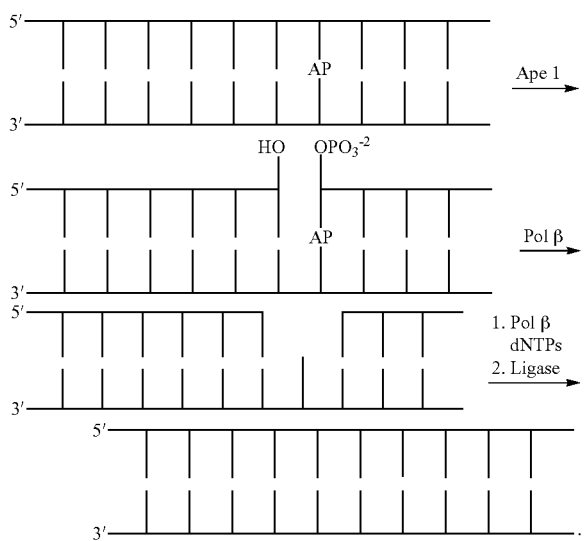

The enzyme excises the 5'-phosphorylated 2-deoxyribose (dRP) produced upon Ape1 incision of DNA containing an AP site (Scheme 2). Lys72 is the primary amine responsible for Schiff base formation, although the enzyme retains some lyase activity when this amino acid is mutated (Deterding et al., 2000; Prasad et al., 2005; Prasad et al., 1998; Feng et al., 1998). Lys84, which also is present in the lyase active site, is postulated to substitute for Lys72 in the mutated enzyme, albeit with much lower efficiency. Following Schiff base formation, dRP elimination leaves a single nucleotide gap that contains the appropriate end groups for DNA synthesis (by Pol β) and ligation to complete repair (Scheme 1, above).

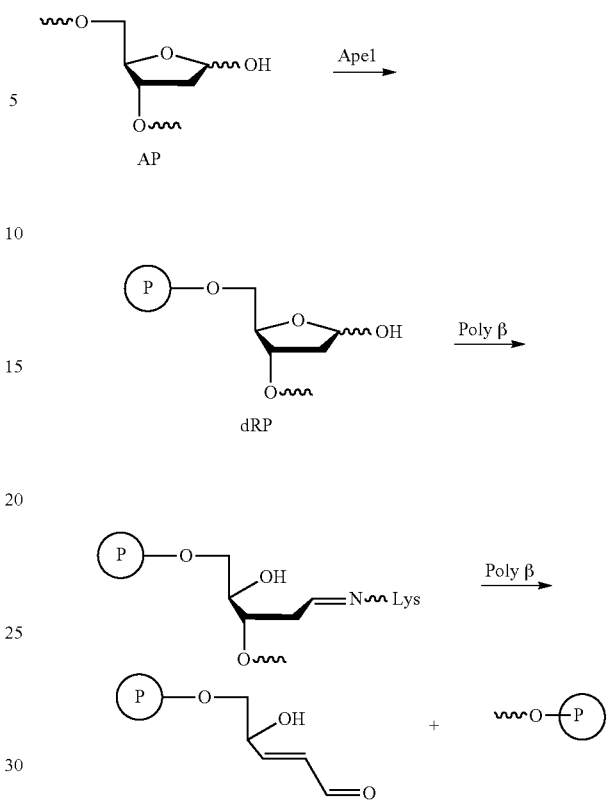

Scheme 2. Role of Pol β in excising the dRP produced upon Ape1 incision of DNA containing an AP site.

Part of the attraction of Pol β as a potential therapeutic target is that it is over expressed in a variety of cancer cells (Husain et al., 1999; Starcevic et al., 2004; Barakat et al., 2012). In addition, Pol β variants are found in a large percentage of tumors (Donigan et al., 2012; Nemec et al., 2012; Donigan et al., 2012). Some of the variants exhibit reduced activity and may contribute to tumorigenesis by decreasing genomic stability. In addition, Pol β's vitality to genome integrity is manifested by the observation that cells lacking both alleles of the gene for this enzyme are embryonic lethal, and knocking down Pol β activity sensitizes cells to DNA damaging agents (Horton et al., 2008). Consequently, Pol β has attracted interest as a target for antitumor therapy. Inhibiting Pol β potentiates the cytotoxic effects of DNA damaging agents and can be cytotoxic in its own right.

Natural and unnatural products have been tested as inhibitors of Pol β and the related enzyme, Pol λ, which is believed to act as a back up for Pol β in BER (Braithwaite et al., 2010; Braithwaite et al., 2005; Gao et al., 2008; Nakamura et al., 2007; Strittmatter et al., 2011; Wilson et al., 2010). Some of these molecules are believed to target the lyase domain. There is an interaction between Pol β and a DNA lesion, dioxobutane (DOB), which is produced by a family of potent cytotoxic antitumor antibiotics following C5'-hydrogen atom abstraction (Pitié and Pratviel, 2010; Goldberg, 1991). DOB efficiently inactivates Pol β (and Pol λ) (Guan and Greenberg, 2010; Guan et al., 2010; Stevens et al., 2013). Radiolabeling experiments, liquid chromatography, and mass spectral analyses of protease digests indicate that the 1,4-dicarbonyl inactivates Pol β in two ways (Scheme 3).

Scheme 3. Inactivation of Pol β by DOB

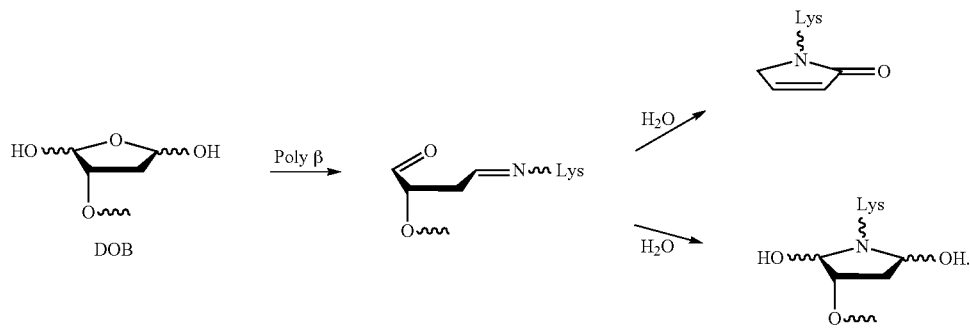

DOB forms a stable lactam following condensation with Lys72 or Lys84, elimination, and dehydration. The lesion also forms a stable adduct without undergoing DNA cleavage. The pC4-AP that is produced upon Ape1 incision of C4-AP (structures below) also contains a 1,4-dicarbonyl and inactivates Pol β and Pol λ (Stevens et al., 2013; Jacobs et al., 2011).

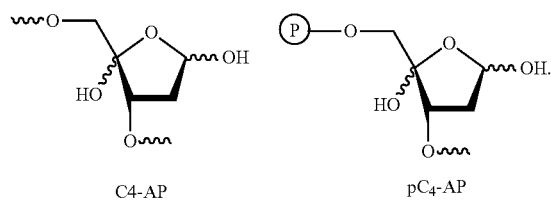

C4-AP      pC₄-AP

SUMMARY

In some aspects, the presently disclosed subject matter provides a compound of formula (I):

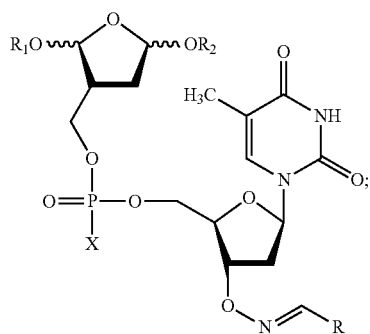

(I)

wherein: X is selected from the group consisting of alkyl, alkoxyl, O⁻, and S⁻; R is selected from the group consisting of substituted or unsubstituted alkyl, heteroalkyl, cycloalkyl, cycloalkylalkyl, cycloheteroalkyl, aryl, heteroaryl, arylalkyl, heteroarylalkyl, multicyclic aliphatic ring systems, multicylic aromatic ring systems, fused aliphatic ring systems, fused aromatic ring systems, and combinations thereof; $R_1$ and $R_2$ are each independently selected from the group consisting of hydrogen and —(=O)-alkyl; and pharmaceutically acceptable salts thereof.

In other aspects, the presently disclosed subject matter provides a method for irreversibly inhibiting a DNA repair enzyme that possesses lyase activity in a subject, the method comprising administering to the subject a therapeutically effective amount of a compound of Formula (I) and pharmaceutically acceptable salts thereof.

In yet other aspects, the presently disclosed subject matter provides a method for inhibiting a cancer cell, the method comprising contacting the cancer or noncancerous cell with a compound of Formulae (I) in an amount effective to irreversibly inhibit a DNA repair enzyme that possesses lyase activity.

In still yet other aspects, the presently disclosed subject matter provides a method for irreversibly inhibiting a DNA repair enzyme that possesses lyase activity, the method comprising contacting the DNA repair enzyme with a compound of Formula (I) wherein contacting the DNA repair enzyme with the compound irreversibly inhibits the DNA repair enzyme.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1:
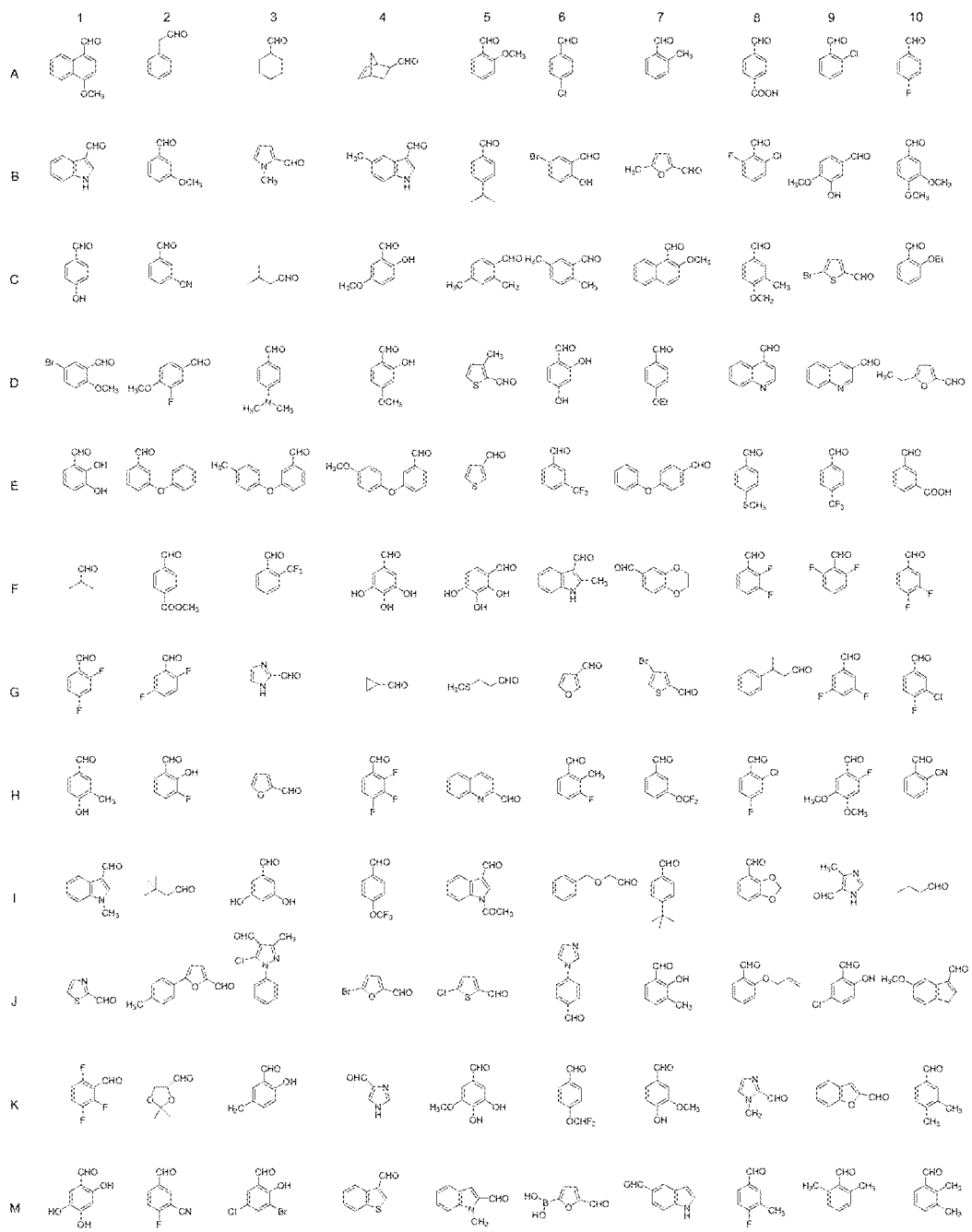
Figure 1:
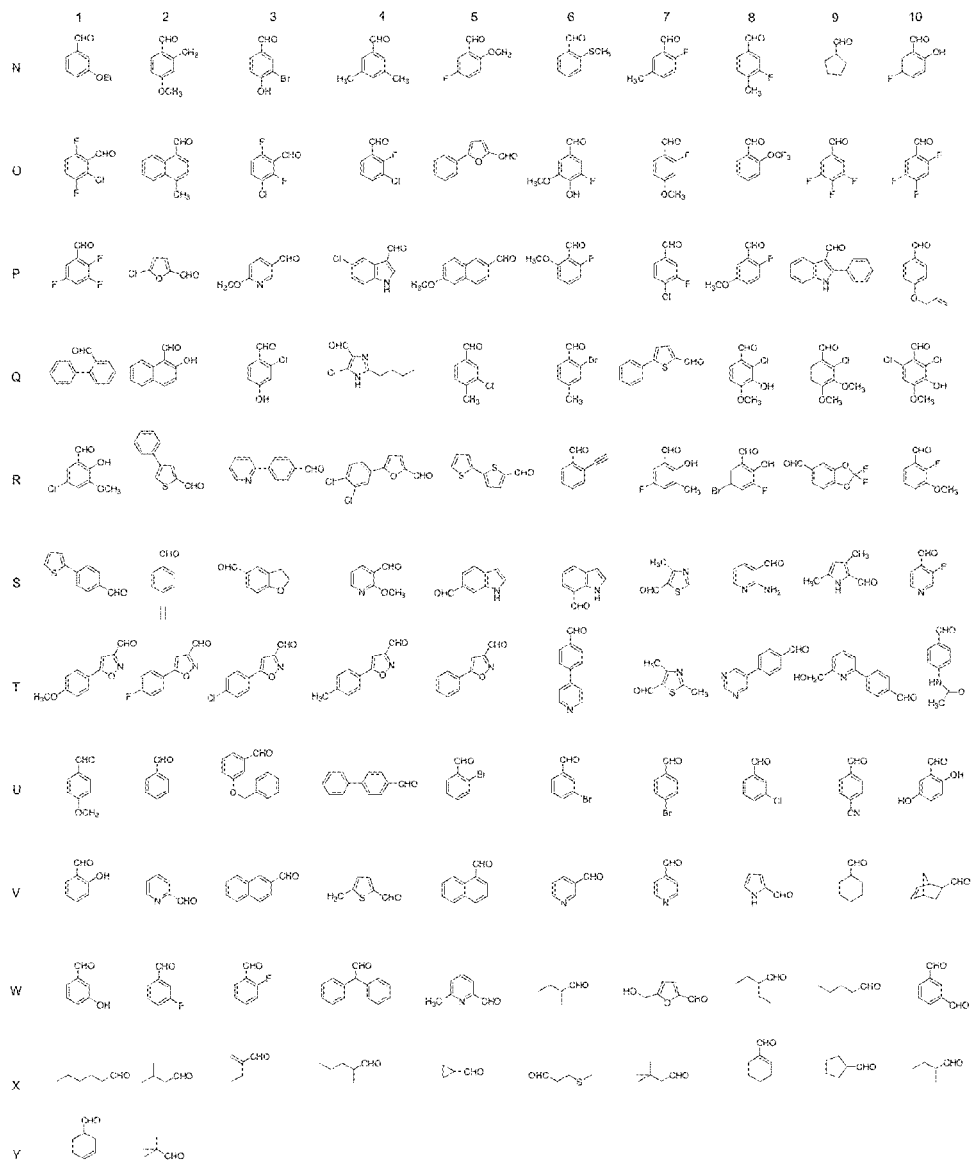
Figure 2:
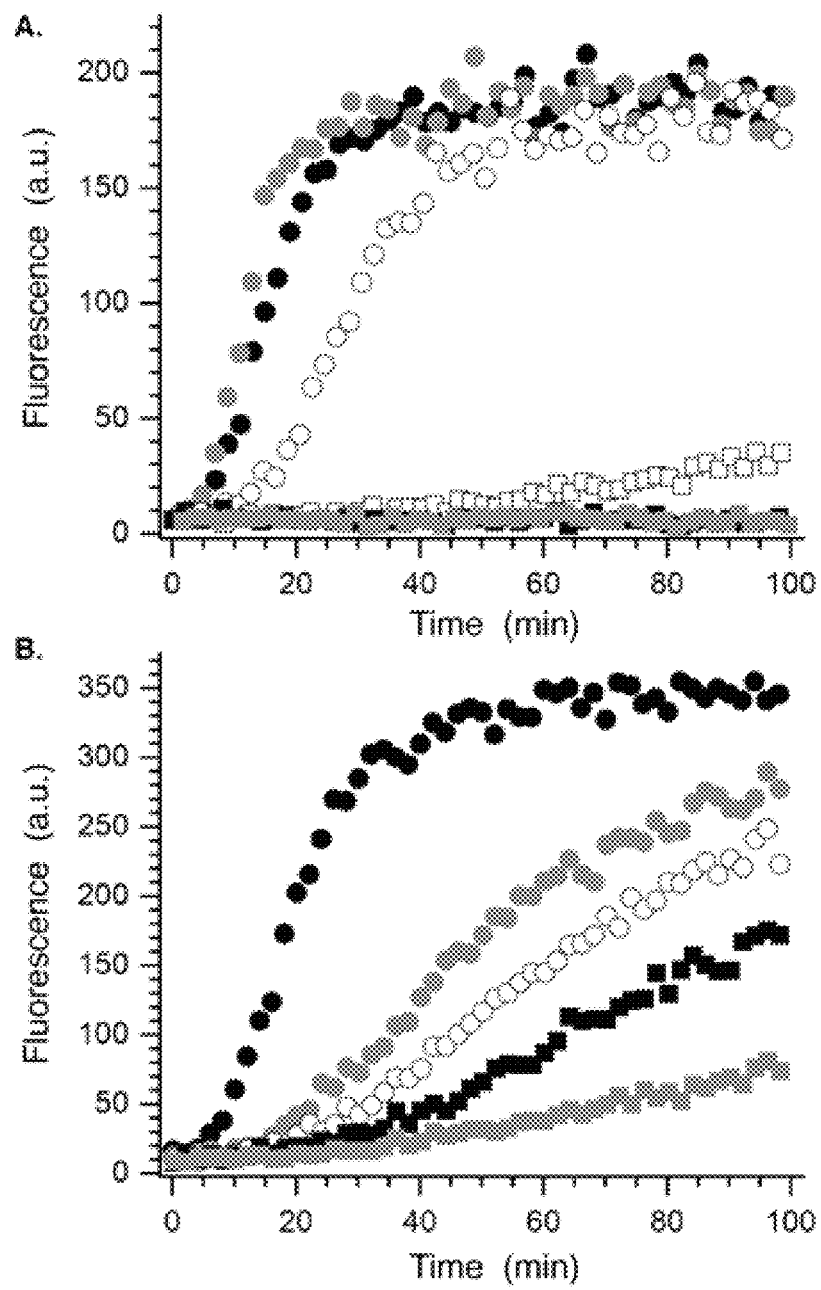
Figure 3:
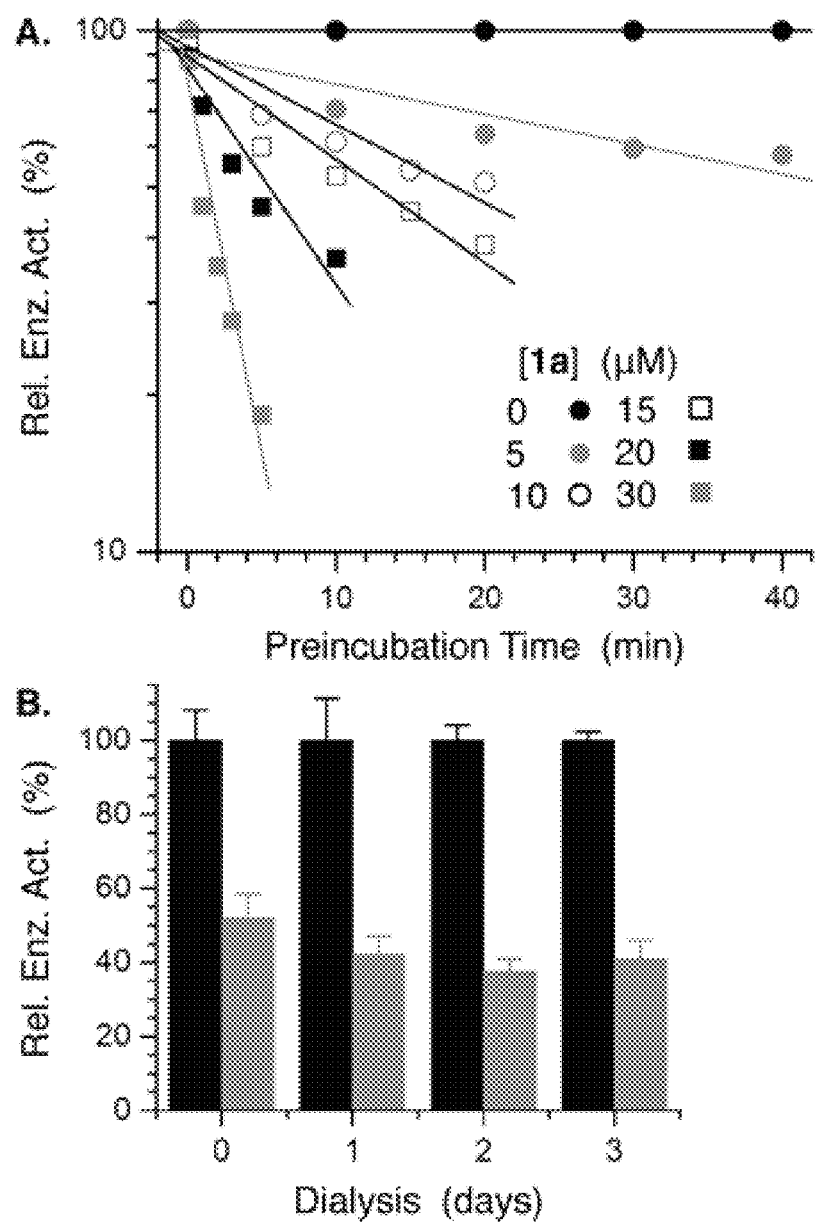
Figure 4:
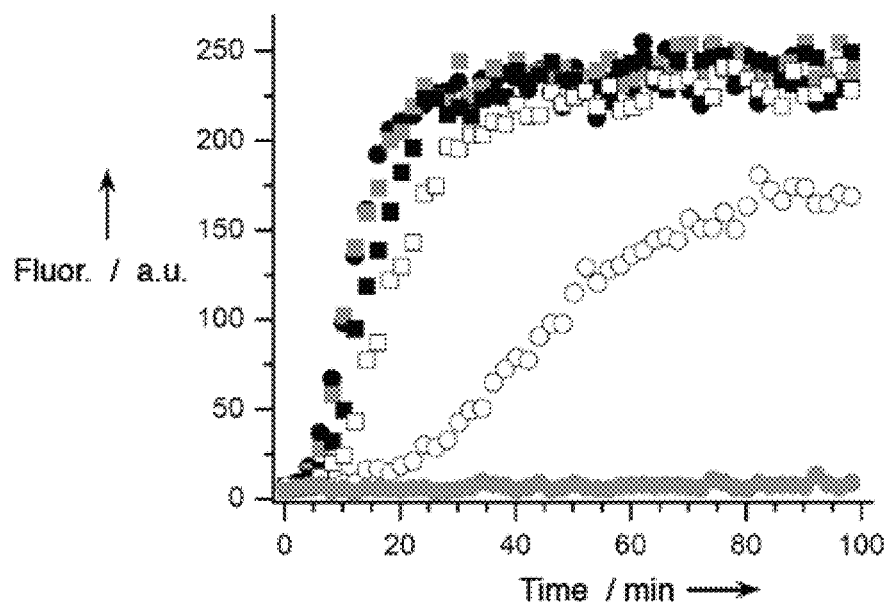

Having thus described the presently disclosed subject matter in general terms, reference will now be made to the accompanying Figures, which are not necessarily drawn to scale, and wherein:

FIG. 1 shows the structures of the aldehydes used to prepare the oxime library;

FIG. 2 shows inhibition of strand displacement synthesis in 13 by 1a: (A) dependence on [1a](μM): 0, ●; 1, ●; 5, ○; 10, □; 25, ■; 50, ■; and (B) dependence on preincubation time of 1a (10 μM) with Pol β: no inhibitor, ●; preincubation time (min): 5, ●; 20, ○; 40, ■; 60, ■:

FIG. 3 shows irreversible inhibition of Pol β by 1a: (A) relative Pol β lyase activity on $^{32}$P-15 as a function of [1a] and preincubation time of inhibitor with enzyme; and (B) normalized lyase activity of Pol β on $^{32}$P-15 upon dialysis following incubation with or without 1a; [1a](μM): 0, ■; 50, ■;

FIG. 4 shows the concentration dependence of Pol β strand displacement synthesis inhibition by 2a; [2a] (μM): 0, ●; 1, ■; 5, ■; 10, □; 25, ○; 50, ●

Figure 5:
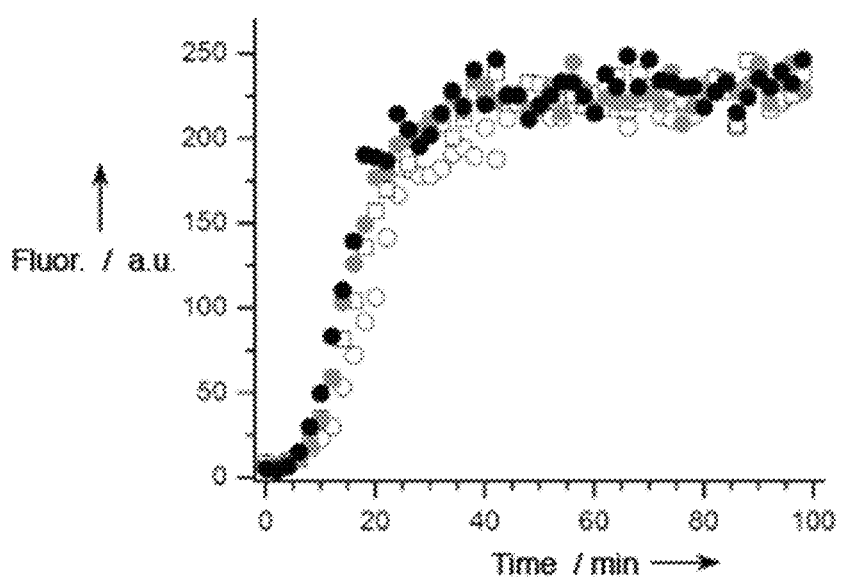
Figure 6:
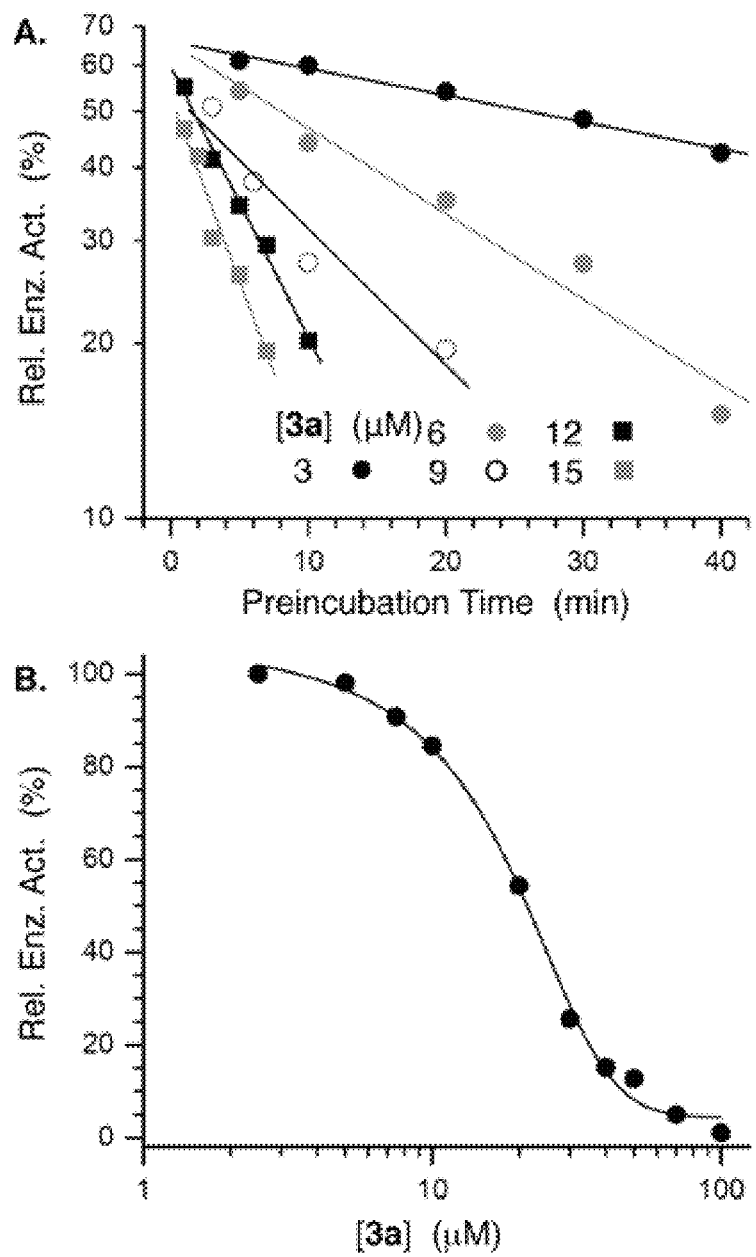
Figure 7:
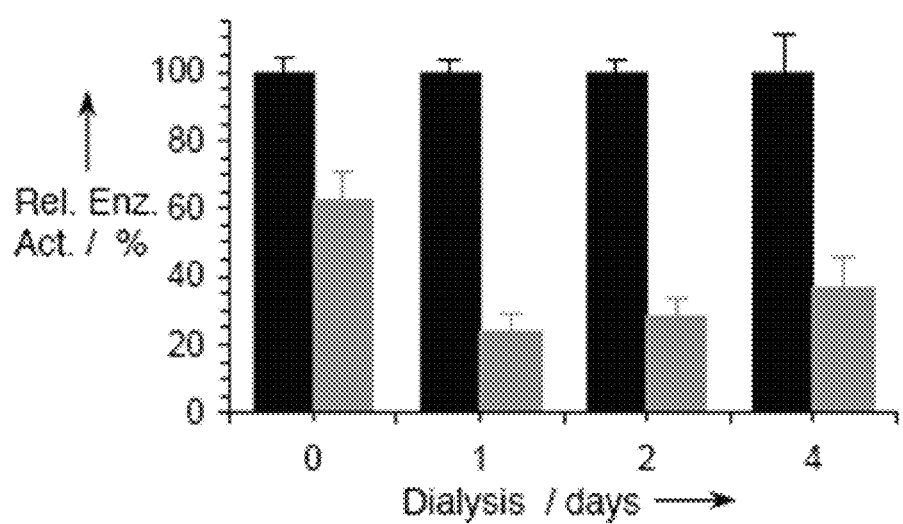
Figure 8:
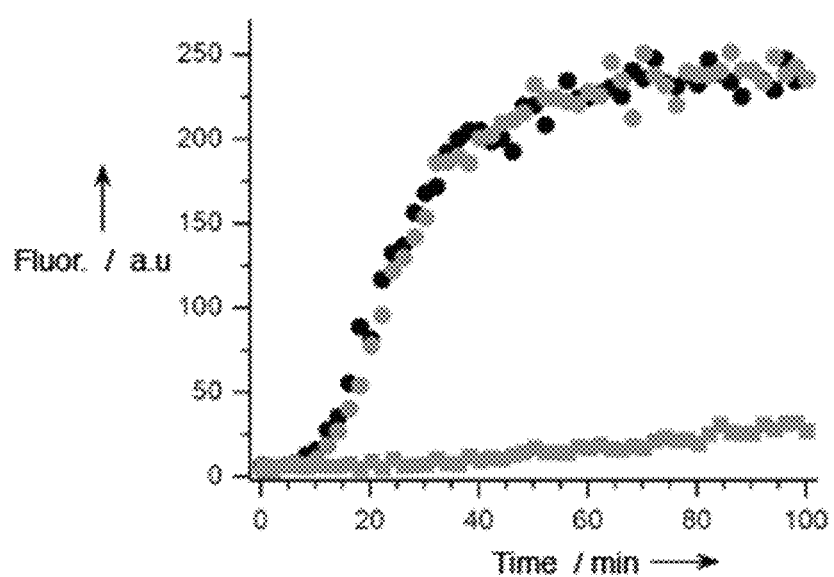
Figure 9:
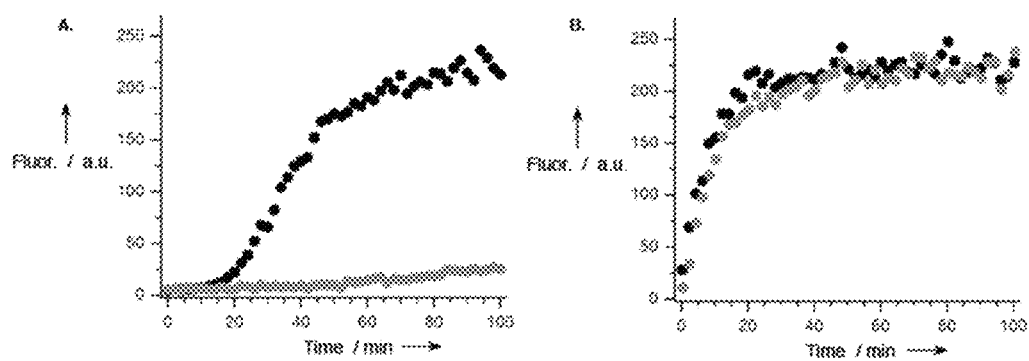
Figure 10:
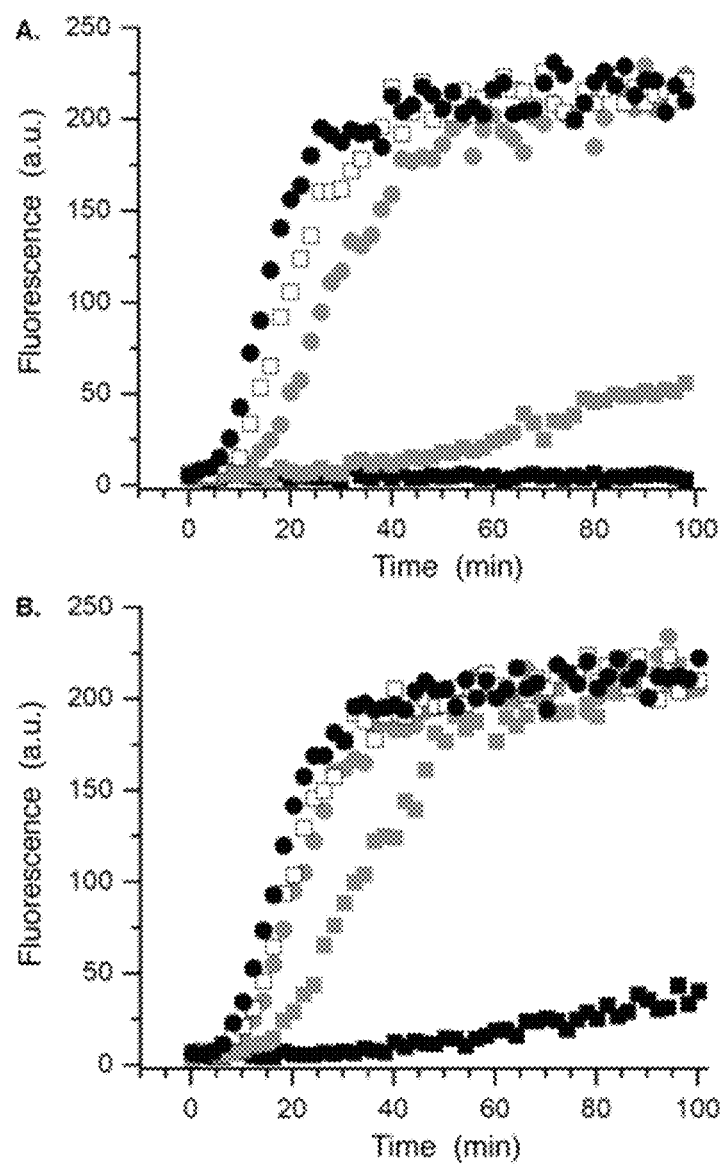
Figure 11:
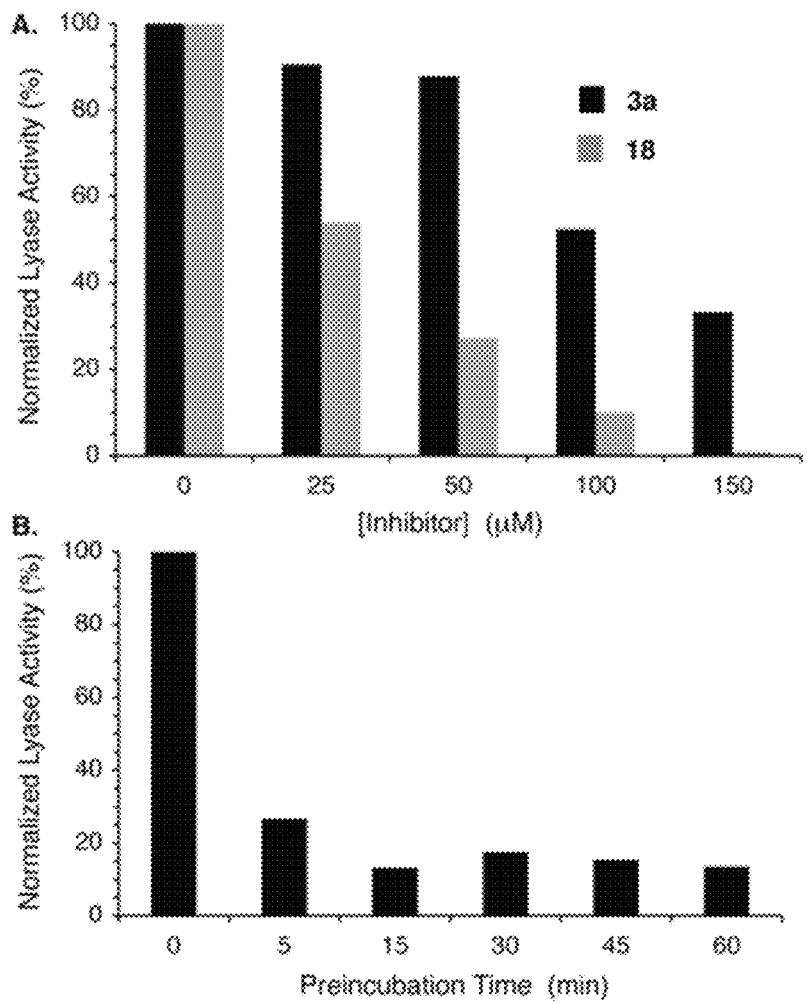
Figure 12:
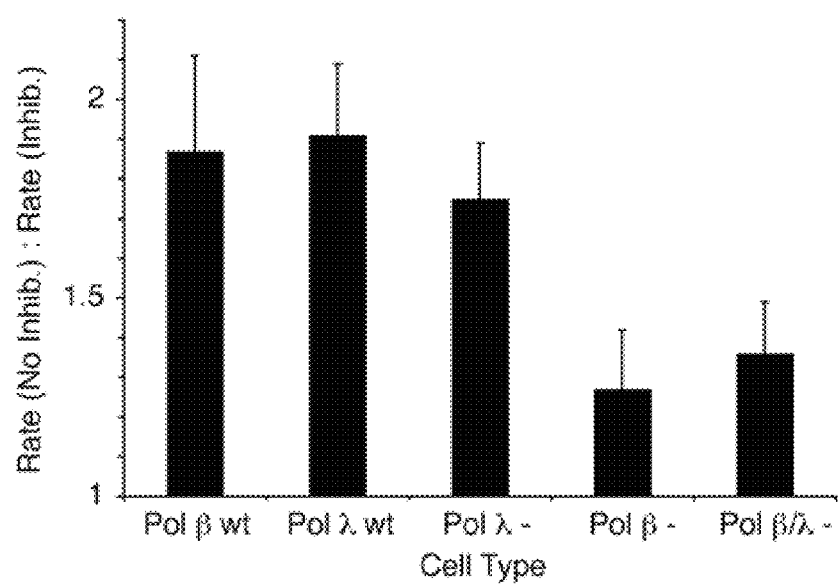
Figure 13:
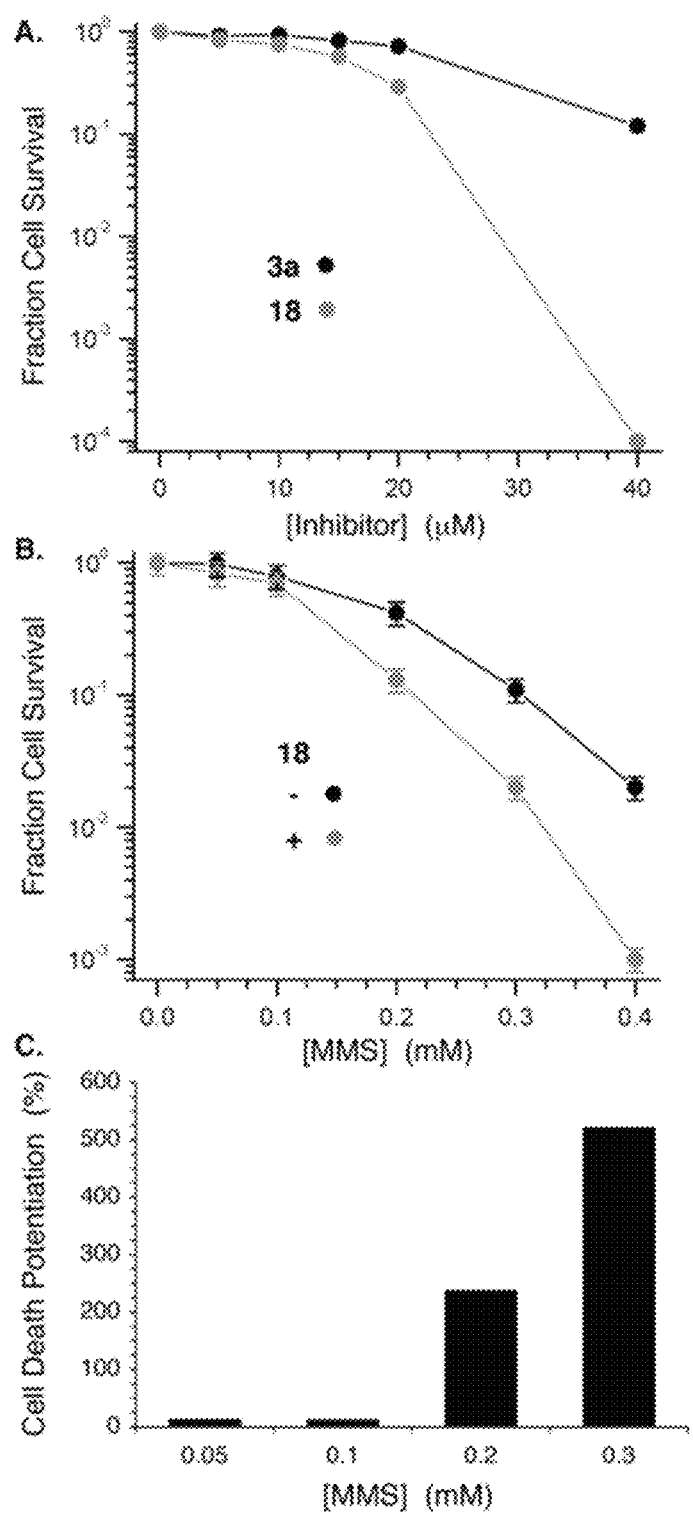

FIG. 5 shows the concentration dependence of Pol β strand displacement synthesis inhibition by 16; [16] (μM): 0, ●; 25, ●; 50, □; 150, ○;

FIG. 6 shows irreversible inhibition of Pol β by 3a: (A) relative Pol β lyase activity on $^{32}$P-15 as a function of [3a] and preincubation time of inhibitor with enzyme; and (B) $IC_{50}$ of Pol β inactivation following 30 min preincubation with 3a;

FIG. 7 shows the relative Pol β activity with and without 3a following dialysis; 0 μM, ■; 20 μM, ■;

FIG. 8 shows Pol β polymerase activity in the absence of inhibitor and the presence of 3a or its reduced form, 17; no inhibitor, ●; 17, 20 μM, ●; 3a, 20 μM, ■;

FIG. 9 shows the selectivity for Pol β inhibition by 3a: (A) effect on Pol β; and (B) effect on Klenow exo⁻. [3a] (μM), 0, ●; 10, ●;

FIG. 10 shows the effect of glutathione (GSH) on Pol β inhibition by 1a: (A) no GSH; and (B) [GSH]=5 mM. [1a] (μM); 0, ●; 5, □; 10, ●; 25, ■; 50, ■;

FIG. 11 shows the effect of 3a and proinhibitor 18 on DU145 lysate lyase activity: (A) comparison of 3a and 18 as a function of concentration; preincubation time: 1 h, [$^{32}$P-15]= 200 nM; and (B) effect of preincubation time on the ability of 18 (50 μM) to inhibit lyase activity;

FIG. 12 shows the effect of proinhibitor 18 (50 μM) on lyase activity (3'-$^{32}$P-15) of various cell lysates from mouse embryonic fibroblasts; and FIG. 13 shows the effect of 3a and proinhibitor 18 on DU145 prostate cancer cells: (A) survival fraction as a function of inhibitor concentration; and (B) effect of 18 (20 μM) on methyl methanesulfonate (MMS) cytotoxicity; and (C) potentiation of MMS cytotoxicity by 18 (20 μM).

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Irreversible Inhibitors of DNA Polymerase Beta

The presently disclosed subject matter provides DNA repair enzyme inhibitors that irreversibly inactivate a DNA repair enzyme. In some embodiments, irreversible inactivation occurs by targeting the lyase active site of the DNA repair enzyme. In particular embodiments, the DNA repair enzyme is DNA polymerase β (Guan and Greenberg, 2010; Guan et al., 2010; Stevens et al., 2013; Jacobs et al., 2011). It is believed that the presently disclosed subject matter represents the first example of an irreversible inhibitor that targets the lyase domain of DNA polymerase β.

As used herein, the term "DNA repair enzyme" includes an enzyme that can repair changes or mutations in DNA and restore the DNA to its original state. The presently disclosed method is applicable for various DNA repair enzymes that possess lyase activity. As used herein, the term "lyase activity" means an activity that involves the removal of a group from a double bond or the addition of a group to a double bond. Accordingly, in some embodiments, the compound inhibits the lyase activity of the DNA repair enzyme.

Non-limiting examples of DNA repair enzymes suitable for use with the presently disclosed methods include DNA polymerase β (UniProt Accession No. P06746, for example), 5'-deoxyribose-5-phosphate lyase Ku70 (UniProt Accession No. P12956, for example), Endonuclease III-like protein 1(UniProt Accession No. P78549, for example), DNA polymerase λ, and the like. In some embodiments, the DNA repair enzyme is selected from the group consisting of DNA polymerase β, 5'-deoxyribose-5-phosphate lyase Ku70, and Endonuclease III-like protein 1.

Accordingly, the presently disclosed subject matter provides a compound of formula (I):

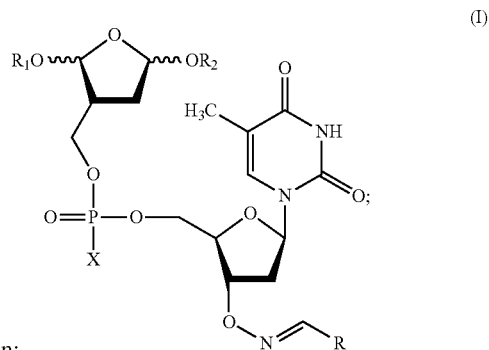

wherein:

X is selected from the group consisting of alkyl, alkoxyl, O⁻, and S⁻; R is selected from the group consisting of substituted or unsubstituted alkyl, heteroalkyl, cycloalkyl, cycloalkylalkyl, cycloheteroalkyl, aryl, heteroaryl, arylalkyl, heteroarylalkyl, multicyclic aliphatic ring systems, multicylic aromatic ring systems, fused aliphatic ring systems, fused aromatic ring systems, and combinations thereof;

$R_1$ and $R_2$ are each independently selected from the group consisting of hydrogen and —(=O)-alkyl; and pharmaceutically acceptable salts thereof.

In some embodiments, R is selected from the group consisting of a substituent group provided in FIG. 1. In particular embodiments, the compound of formula (I) is selected from the group consisting of:

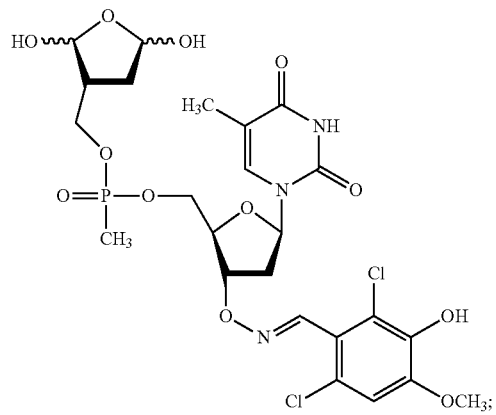

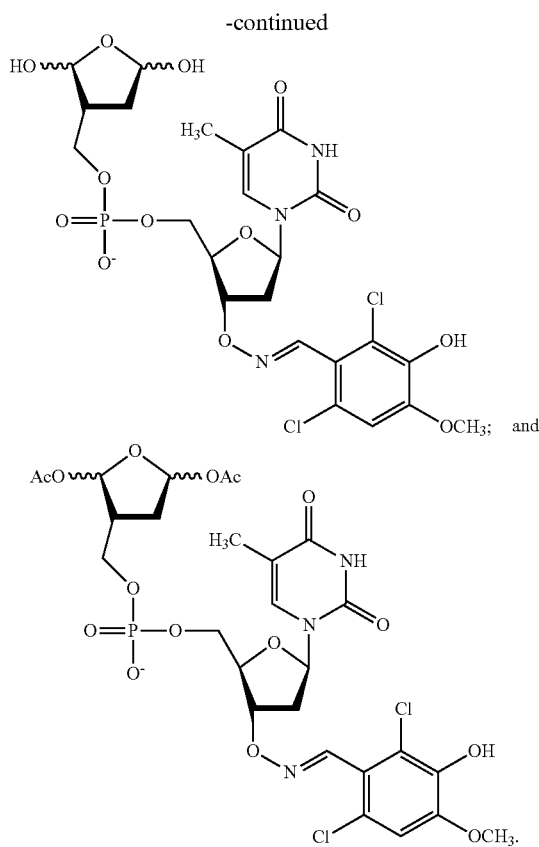

In other embodiments, the presently disclosed subject matter provides a method for irreversibly inhibiting a DNA repair enzyme that possesses lyase activity in a subject, the method comprising administering to the subject a therapeutically effective amount of a compound of Formula (I).

As used herein, the term "inhibit" or "inhibits" has at least two meanings. It may mean to decrease, suppress, attenuate, diminish, arrest, or stabilize the development or progression of a disease, disorder, or condition, the activity of a biological pathway, or a biological activity such as cancer, e.g., by at least 10%, 20%, 30%, 40%, 50%, 60%, 70%, 80%, 90%, 95%, 98%, 99%, or even 100% compared to an untreated control subject, cell, biological pathway, or biological activity. It will be appreciated that, although not precluded, treating a disease, disorder or condition does not require that the disease, disorder, condition or symptoms associated therewith be completely eliminated. The term "inhibit" or "inhibits" may also mean to decrease, suppress, attenuate, diminish, or arrest the activity of an enzyme, which is a biological molecule that accelerates both the rate and specificity of a metabolic reaction. An "inhibitor" is a molecule that inhibits the activity of an enzyme. An "irreversible inhibitor" usually covalently modifies an enzyme and therefore the inhibition cannot be reversed. Irreversible inhibitors may act at, near, or remote from the active site of an enzyme.

In some embodiments, the subject has cancer. A "cancer" in a subject refers to the presence of cells possessing characteristics typical of cancer-causing cells, for example, uncontrolled proliferation, loss of specialized functions, immortality, significant metastatic potential, significant increase in anti-apoptotic activity, rapid growth and proliferation rate, and certain characteristic morphology and cellular markers. A cancer can include, but is not limited to, head cancer, neck cancer, head and neck cancer, lung cancer, breast cancer, prostate cancer, colorectal cancer, esophageal cancer, stomach cancer, leukemia/lymphoma, uterine cancer, skin cancer, endocrine cancer, urinary cancer, pancreatic cancer, gastrointestinal cancer, ovarian cancer, cervical cancer, and adenomas.

Without wishing to be bound to any one particular theory, it is believed that knocking down Pol β activity can be cytotoxic to a cancer cell. Therefore, in some embodiments, inhibiting the DNA repair enzyme treats, inhibits, delays, or prevents the spread of the cancer in the subject. In other embodiments, the method further comprises treating, inhibiting, delaying, or preventing the spread of the cancer by inhibiting at least one cancer cell involved in one or more biological processes selected from the group consisting of cell migration, cell growth, cell adhesion, angiogenesis, cancer cell invasion, apoptosis, tumor formation, tumor progression, metastasis, degradation of the extracellular matrix, pericellular proteolysis, activation of plasminogen, and changes in the levels of an extracellular protease.

In some embodiments, the presently disclosed subject matter provides a method for inhibiting a cancer cell, the method comprising contacting the cancer or noncancerous cell with a compound of Formula (I) in an amount effective to irreversibly inhibit a DNA repair enzyme that possesses lyase activity.

The presently disclosed methods may further comprise administering to the subject a DNA damaging agent. A "DNA damaging agent" is an agent that damages the DNA structure in some way, such as causing damage in the DNA bases or its sugar phosphate backbone or causing the formation of covalent bonds between the DNA and at least one protein. The DNA damage may affect DNA-histone and DNA-transcription factor interactions and may impact DNA packing, cell division, replication and/or transcription of the DNA.

It has been found herein below that the presently disclosed compounds potentiate the cytotoxicity of a DNA damaging agent whose effects would require repair by Pol β. In some embodiments, the DNA damaging agent is methyl methanesulfonate (MMS). In other embodiments, the DNA damaging agent is administered before, simultaneously, or after administration of the compound of Formula (I), or combinations thereof. A DNA damaging agent may include, for example, an agent that alkylates DNA or oxidatively damages DNA.

In some embodiments, the presently disclosed method comprises a method for irreversibly inhibiting a DNA repair enzyme that possesses lyase activity in a cell, the method comprising contacting the cell comprising the DNA repair enzyme with a compound of Formula (I), wherein contacting the cell with the compound irreversibly inhibits the DNA repair enzyme.

By "contacting", it is meant any action that results in a therapeutically effective amount of at least one presently disclosed compound physically contacting at least one cell comprising a DNA repair enzyme. The method can be practiced in vitro or ex vivo by introducing, and preferably mixing, the compound and cell comprising a DNA repair enzyme in a controlled environment, such as a culture dish or tube. The method can be practiced in vivo, in which case contacting means exposing at least one cell comprising a DNA repair enzyme in a subject to a therapeutically effective amount of at least one compound of the presently disclosed subject matter, such as administering the compound to a subject via any suitable route. According to the presently disclosed subject matter, contacting may comprise introducing, exposing, and the like, the compound at a site distant to the cell comprising a DNA repair enzyme to be contacted, and allowing the bodily functions of the subject, or natural (e.g., diffusion) or man-induced (e.g., swirling) movements of fluids to result in contact of the compound and cell comprising a DNA repair enzyme(s). In some embodiments, the method may inhibit a DNA repair enzyme in vitro, in vivo, or ex vivo.

In some embodiments, the presently disclosed method further comprises contacting the cell comprising a DNA repair enzyme with a DNA damaging agent. In other embodiments, the DNA damaging agent is methyl methanesulfonate (MMS).

In other embodiments, the presently disclosed subject matter provides a pharmaceutical composition including one compound of formula (I), alone or in combination with one or more additional therapeutic agents in admixture with a pharmaceutically acceptable excipient. One of skill in the art will recognize that the pharmaceutical compositions include the pharmaceutically acceptable salts of the compounds described above.

In therapeutic and/or diagnostic applications, the compounds of the disclosure can be formulated for a variety of modes of administration, including systemic and topical or localized administration. Techniques and formulations generally may be found in Remington: The Science and Practice of Pharmacy ($20^{th}$ ed.) Lippincott, Williams & Wilkins (2000).

The compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A non-limiting dosage is 10 to 30 mg per day. The exact dosage will depend upon the route of administration, the form in which the compound is administered, the subject to be treated, the body weight of the subject to be treated, and the preference and experience of the attending physician.

Pharmaceutically acceptable salts are generally well known to those of ordinary skill in the art, and may include, by way of example but not limitation, acetate, benzenesulfonate, besylate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy ($20^{th}$ ed.) Lippincott, Williams & Wilkins (2000). Pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate.

Depending on the specific conditions being treated, such agents may be formulated into liquid or solid dosage forms and administered systemically or locally. The agents may be delivered, for example, in a timed- or sustained-low release form as is known to those skilled in the art. Techniques for formulation and administration may be found in Remington: The Science and Practice of Pharmacy ($20^{th}$ ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intra-sternal, intra-synovial, intra-hepatic, intralesional, intracranial, intraperitoneal, intranasal, or intraocular injections or other modes of delivery.

For injection, the agents of the disclosure may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure also may be formulated by methods known to those of skill in the art, and may include, for example, but not limited to, examples of solubilizing, diluting, or dispersing substances such as, saline, preservatives, such as benzyl alcohol, absorption promoters, and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Depending upon the particular condition, or disease state, to be treated or prevented, additional therapeutic agents, which are normally administered to treat or prevent that condition, may be administered together with the inhibitors of this disclosure. For example, chemotherapeutic agents or other antiproliferative agents may be combined with the inhibitors of this disclosure to treat proliferative diseases and cancer. Examples of known chemotherapeutic agents include, but are not limited to, adriamycin, dexamethasone, vincristine, cyclophosphamide, fluorouracil, topotecan, taxol, interferons, and platinum derivatives.

The additional agents may be administered separately, as part of a multiple dosage regimen, from the inhibitor-containing composition. Alternatively, these agents may be part of a single dosage form, mixed together with the inhibitor in a single composition.

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to compounds of formula I are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted, for example, with fluorine at one or more positions).

Where substituent groups or linking groups are specified by their conventional chemical formulae, written from left to right, they equally encompass the chemically identical substituents that would result from writing the structure from right to left, e.g., —CH$_2$O— is equivalent to —OCH$_2$—; —C(=O)O— is equivalent to —OC(=O)—; —OC(=O)NR— is equivalent to —NRC(=O)O—, and the like.

When the term "independently selected" is used, the substituents being referred to (e.g., R groups, such as groups $R_1$, $R_2$, and the like, or variables, such as "m" and "n"), can be identical or different. For example, both $R_1$ and $R_2$ can be substituted alkyls, or $R_1$ can be hydrogen and $R_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Description of compounds of the present disclosure is limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, isopropyl, cyclopropyl, allyl, vinyl, n-butyl, tert-butyl, ethynyl, cyclohexyl, methoxy, diethylamino, and the like.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., $C_1$-$C_{10}$ means one to ten carbons). In particular embodiments, the term "alkyl" refers to $C_{1-20}$ inclusive, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, iso-pentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "heteroalkyl," by itself or in combination with another term, means, unless otherwise stated, a stable straight or branched chain, or cyclic hydrocarbon group, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, $-CH_2-CH_2-O-CH_3$, $-CH_2-CH_2-NH-CH_3$, $-CH_2-CH_2-N(CH_3)-CH_3$, $-CH_2-S-CH_2-CH_3$, $-CH_2-CH_2-S(O)-CH_3$, $-CH_2-CH_2-S(O)_2-CH_3$, $-CH=CH-O-CH_3$, $-Si(CH_3)_3$, $-CH_2-CH=N-OCH_3$, $-CH=CH-N(CH_3)-CH_3$, $O-CH_3$, $-O-CH_2-CH_3$, and $-CN$. Up to two or three heteroatoms may be consecutive, such as, for example, $-CH_2-NH-OCH_3$ and $-CH_2-O-Si(CH_3)_3$.

As described above, heteroalkyl groups, as used herein, include those groups that are attached to the remainder of the molecule through a heteroatom, such as $-C(O)R'$, $-C(O)NR'$, $-NR'R''$, $-OR'$, $-SR$, and/or $-SO_2R'$. Where "heteroalkyl" is recited, followed by recitations of specific heteroalkyl groups, such as $-NR'R$ or the like, it will be understood that the terms heteroalkyl and $-NR'R''$ are not redundant or mutually exclusive. Rather, the specific heteroalkyl groups are recited to add clarity. Thus, the term "heteroalkyl" should not be interpreted herein as excluding specific heteroalkyl groups, such as $-NR'R''$ or the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl, and fused ring systems, such as dihydro- and tetrahydronaphthalene, and the like.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl."

More particularly, the term "alkenyl" as used herein refers to a monovalent group derived from a $C_{1-20}$ inclusive straight or branched hydrocarbon moiety having at least one carbon-carbon double bond by the removal of a single hydrogen atom. Alkenyl groups include, for example, ethenyl (i.e., vinyl), propenyl, butenyl, 1-methyl-2-buten-1-yl, pentenyl, hexenyl, octenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{1-20}$ hydrocarbon of a designed number of carbon atoms containing at least one carbon-carbon triple bond. Examples of "alkynyl" include ethynyl, 2-propynyl (propargyl), 1-propynyl, pentynyl, hexynyl, heptynyl, and allenyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—($CH_2$)$_3$—); cyclohexylene (—$C_6H_{10}$—); —CH=CH—CH=CH—; —CH=CH—$CH_2$—; —$CH_2CH_2CH_2CH_2$—, —$CH_2$CH=CHCH$_2$—, —$CH_2$CsCCH$_2$—, —$CH_2CH_2CH(CH_2CH_2CH_3)CH_2$—, —($CH_2$)$_q$—N(R)—($CH_2$)$_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—($CH_2$)$_2$—O—). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—.

The term "aryl" means, unless otherwise stated, an aromatic hydrocarbon substituent that can be a single ring or multiple rings (such as from 1 to 3 rings), which are fused together or linked covalently.

The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

For brevity, the term "aryl" when used in combination with other terms (e.g., aryloxo, arylthioxo, arylalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g. "3 to 7 membered"), the term "member" refers to a carbon or heteroatom.

Further, a structure represented generally by the formula:

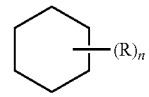

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

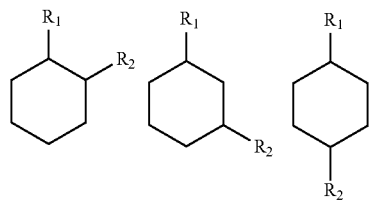

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

The symbol ( ⁓⁓⁓ ) denotes the point of attachment of a moiety to the remainder of the molecule.

When a named atom of an aromatic ring or a heterocyclic aromatic ring is defined as being "absent," the named atom is replaced by a direct bond.

Each of above terms (e.g., "alkyl," "heteroalkyl," "cycloalkyl, and "heterocycloalkyl", "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R''', —OC(O)R', —C(O)R', —CO$_2$R', —C(O)NR'R", —OC(O)NR'R", —NR"C(O)R', —NR'—C(O)NR"R''', —NR"C(O)OR', —NR—C(NR'R")=NR''', —S(O)R', —S(O)$_2$R', —S(O)$_2$NR'R", —NRSO$_2$R', —CN and —NO$_2$ in a number ranging from zero to (2 m'+1), where m' is the total number of carbon atoms in such groups. R', R", R''' and R'''' each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R", R''' and R'''' groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl groups above, exemplary substituents for aryl and heteroaryl groups (as well as their divalent derivatives) are varied and are selected from, for example: halogen, —OR', —NR'R", —SR', -halogen, —SiR'R"R''', —OC(O)R', —C(O)R', —CO$_2$R', —C(O)NR'R", —OC(O)NR'R", —NR"C(O)R', —NR'—C(O)NR"R''', —NR"C(O)OR', —NR—C(NR'R"R''')=NR'''', —NR—C(NR'R")=NR'''—S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxo, and fluoro (C$_1$-C$_4$)alkyl, in a number ranging from zero to the total number of open valences on aromatic ring system; and where R', R", R''' and R'''' may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R''' and R'''' groups when more than one of these groups is present.

Two of the substituents on adjacent atoms of aryl or heteroaryl ring may optionally form a ring of the formula -T-C(O)—(CRR')$_q$-U-, wherein T and U are independently —NR—, —O—, —CRR'—or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R''')$_d$—, where s and d are independently integers of from 0 to 3, and X' is —O—, —NR'—, —S—, —S(O)—, —S(O)$_2$—, or —S(O)$_2$NR'—. The substituents R, R', R" and R''' may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocylic, heterocyclic, or aromatic heterocyclic group as defined herein). As such, the term "acyl" specifically includes arylacyl groups, such as an acetylfuran and a phenacyl group. Specific examples of acyl groups include acetyl and benzoyl.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include C$_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, t-butoxyl, and n-pentoxyl, neopentoxy, n-hexoxy, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an amide group of the formula —CONH$_2$. "Alkylcarbamoyl" refers to a R'RN—CO— group wherein one of R and R' is hydrogen and the other of R and R' is alkyl and/or substituted alkyl as previously described. "Dialkylcarbamoyl" refers to a R'RN—CO— group wherein each of R and R' is independently alkyl and/or substituted alkyl as previously described.

The term carbonyldioxyl, as used herein, refers to a carbonate group of the formula —O—CO—OR.

"Acyloxyl" refers to an acyl-O— group wherein acyl is as previously described.

The term "amino" refers to the —NH$_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylamino refers to a group having the structure —NR'R"R'", wherein R', R", and R'" are each independently selected from the group consisting of alkyl groups. Additionally, R', R", and/or R'" taken together may optionally be —(CH$_2$)$_k$— where k is an integer from 2 to 6. Examples include, but are not limited to, methylamino, dimethylamino, ethylamino, diethylamino, diethylaminocarbonyl, methylethylamino, iso-propylamino, piperidino, trimethylamino, and propylamino.

The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —(C=O)— group.

The term "carboxyl" refers to the —COOH group. Such groups also are referred to herein as a "carboxylic acid" moiety.

The terms "halo," "halide," or "halogen" as used herein refer to fluoro, chloro, bromo, and iodo groups. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element.

The term "nitro" refers to the —NO$_2$ group.

The term "thio" refers to a compound described previously herein wherein a carbon or oxygen atom is replaced by a sulfur atom.

The term "sulfate" refers to the —SO$_4$ group.

The term thiohydroxyl or thiol, as used herein, refers to a group of the formula —SH.

The term ureido refers to a urea group of the formula —NH—CO—NH$_2$.

Unless otherwise explicitly defined, a "substituent group," as used herein, includes a functional group selected from one or more of the following moieties, which are defined herein:

(A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "lower substituent" or "lower substituent group," as used herein means a group selected from all of the substituents described hereinabove for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_5$-C$_7$ cycloalkyl, and each substituted or unsubstituted heterocycloalkyl is a substituted or unsubstituted 5 to 7 membered heterocycloalkyl.

A "size-limited substituent" or "size-limited substituent group," as used herein means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_4$-C$_8$ cycloalkyl, and each substituted or unsubstituted heterocycloalkyl is a substituted or unsubstituted 4 to 8 membered heterocycloalkyl.

Throughout the specification and claims, a given chemical formula or name shall encompass all tautomers, congeners, and optical- and stereoisomers, as well as racemic mixtures where such isomers and mixtures exist.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those which are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefenic bonds or other centers of geometric asymmetry, and unless specified otherwise, it is intended that the compounds include both E and Z geometric isomers.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present disclosure, whether radioactive or not, are encompassed within the scope of the present disclosure.

As used herein the term "monomer" refers to a molecule that can undergo polymerization, thereby contributing constitutional units to the essential structure of a macromolecule or polymer.

A "polymer" is a molecule of high relative molecule mass, the structure of which essentially comprises the multiple repetition of unit derived from molecules of low relative molecular mass, i.e., a monomer.

As used herein, an "oligomer" includes a few monomer units, for example, in contrast to a polymer that potentially can comprise an unlimited number of monomers. Dimers, trimers, and tetramers are non-limiting examples of oligomers.

The compounds of the present disclosure may exist as salts. The present disclosure includes such salts. Examples of applicable salt forms include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

The term "pharmaceutically acceptable salts" is meant to include salts of active compounds which are prepared with relatively nontoxic acids or bases, depending on the particular substituent moieties found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like {see, for example, Berge et al, "Pharmaceutical Salts", Journal of Pharmaceutical Science, 1977, 66, 1-19). Certain specific compounds of the present disclosure contain both basic and acidic functionalities that allow the compounds to be converted into either base or acid addition salts.

In addition to salt forms, the present disclosure provides compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

Proinhibitors of the compounds described herein are prodrugs that after undergoing chemical changes under physiological conditions, act as inhibitors (molecules that inhibit the activity of an enzyme).

The term "protecting group" refers to chemical moieties that block some or all reactive moieties of a compound and prevent such moieties from participating in chemical reactions until the protective group is removed, for example, those moieties listed and described in T. W. Greene, P. G. M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as tert-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(O)-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups include, but are not limited to the following moieties:

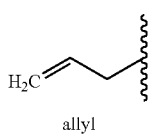
allyl

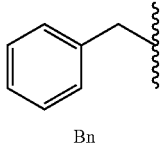
Bn

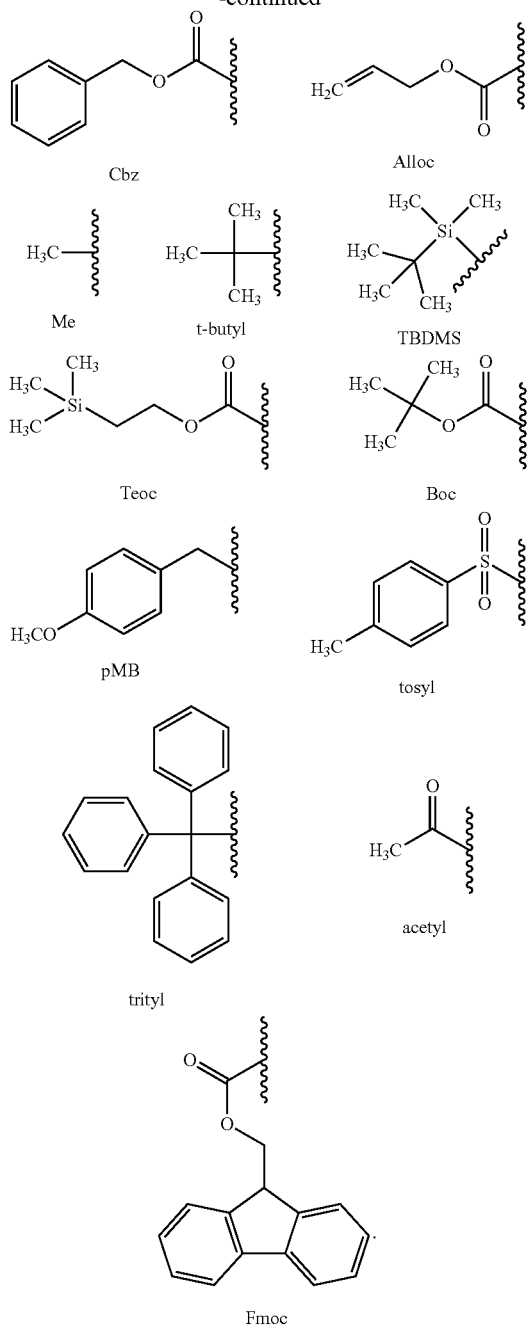

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal (non-human) subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein.

The term "effective amount," as in "a therapeutically effective amount," of a therapeutic agent refers to the amount of the agent necessary to elicit the desired biological response. As will be appreciated by those of ordinary skill in this art, the effective amount of an agent may vary depending on such factors as the desired biological endpoint, the agent to be delivered, the composition of the pharmaceutical composition, the target tissue or cell, and the like. More particularly, the term "effective amount" refers to an amount sufficient to produce the desired effect, e.g., to reduce or ameliorate the severity, duration, progression, or onset of a disease, disorder, or condition (e.g., a disease, condition, or disorder related to cancer), or one or more symptoms thereof; prevent the advancement of a disease, disorder, or condition, cause the regression of a disease, disorder, or condition; prevent the recurrence, development, onset or progression of a symptom associated with a disease, disorder, or condition, or enhance or improve the prophylactic or therapeutic effect(s) of another therapy.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Materials and Methods

General Methods.

Oligonucleotides were synthesized on an Applied Biosystems Incorporated 394 oligonucleotide synthesizer. Oligonucleotide synthesis reagents were purchased from Glen Research (Sterling, Va.). All chemicals were purchased from either Sigma-Aldrich or Fisher and were used without further purification. dNTPs and terminal deoxynucleotide transferase were obtained from New England Biolabs. DNA polymerase β was obtained from Trevigen. α-$^{32}$P-cordycepin was purchased from Perkin Elmer. C18-Sep-Pak cartridges were obtained from Waters. Quantification of radiolabeled oligonucleotides was carried out using a Molecular Dynamics Phosphorimager 840 equipped with ImageQuant Version 5.1 software. Fluorescence data were collected on a Varian Cary Eclipse fluorescence spectrophotometer.

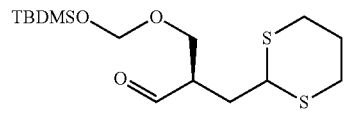

11

Preparation of 11.

To a solution of α,α-diphenylprolinol trimethylsilyl ether catalyst (65.1 mg, 0.2 mmol) at 25° C. in toluene (4 mL) was added solid phosphate buffer pH 7 (50 mg) followed by aqueous formaldehyde solution (250 μL, 3 mmol, 37 wt %). Aldehyde 10 (Kodama and Greenberg, 2005) (177 mg, 1 mmol) was added in one portion to the vigorously stirred suspension and the resulting mixture was stirred for 24 h. The 2 layers were then separated and the toluene was evaporated under reduced pressure (bath temperature <40° C.). The residue was then redissolved in DCM (3 mL) and added to a premixed solution of imidazole (87.5 mg, 1.3 mmol) and TBDMSCl (150 mg, 1.3 mmol) in 2 mL of DCM that had been stirring for 20 min at 0° C. The resulting mixture was stirred for 7 h at 0° C. before concentrating under vacuum. Purification on silica gel using 10% EtOAc in hexanes afforded 105 mg (30%) of 11. $^1$H NMR (CDCl$_3$) δ 9.76-9.75 (m, 1H), 4.87-4.78 (m, 2H), 4.06 (t, J=7.5 Hz, 1H), 3.92-3.73 (m, 2H), 2.96-2.87 (m, 1H), 2.87-2.77 (m, 4H), 2.31 (dt, J=14.8, 7.5 Hz, 1H), 2.16-2.06 (m, 1H), 1.97-1.85 (m, 2H), 0.90 (s, 9H), 0.09 (s, 6H); $^{13}$C NMR (CDCl$_3$) δ 202.3, 90.1, 49.0, 44.6, 31.5, 29.68, 29.67, 25.8, 25.70, 25.69, 18.1, −5.00, −5.01; IR (film) 2928, 2896, 2856, 1726, 1471, 1252, 1115, 1039, 833, 778 cm$^{-1}$; HRMS (M+H$^+$) calcd for C$_{15}$H$_{31}$O$_3$SiS$_2$ 351.1478. found 351.1484.

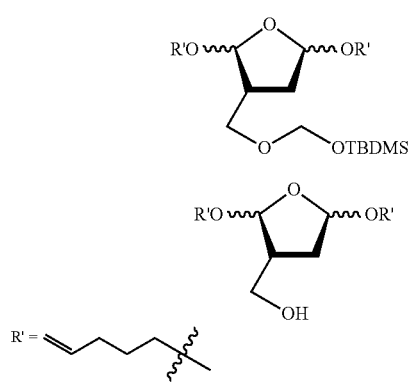

Preparation of 4 via 12.

To a solution of 11 (49.4 mg, 0.14 mmol) and 4-penten-1-ol (120.4 mg, 1.4 mmol) in dry acetonitrile (2 mL) was added Selectfluor™ (147.8 mg, 0.42 mmol) at 25° C. The resulting solution was left to stir overnight. The acetonitrile was evaporated under vacuum and a mixture of Et$_2$O and hexanes (1:10) was added to the residue. The solid was filtered and the filtrate was concentrated under vacuum. The resulting oil was eluted on silica gel with Et$_2$O-hexanes mixture (1:10), affording 12 as an inseparable mixture of isomers. The desilylation was carried out as follows. A solution of TBAF.3H2O (63 mg, 0.2 mmol) in THF (1 mL) was cooled to 0° C. and 12 in THF (1 mL) was added. The resulting mixture was stirred for 2 h at RT. THF was evaporated under vacuum and the column chromatography purification of the residue using as eluent 30% EtOAc in hexanes, resulted in separation of two fractions. (4_fraction1): yield 48% (13.7 mg); $^1$H NMR (CDCl$_3$) δ 5.90-5.72 (m, 2H), 5.23-5.11 (m, 2H), 5.07-4.91 (m, 4H), 3.93-3.62 (m, 4H), 3.48-3.35 (m, 2H), 2.69-2.17 (m, 3H), 2.10 (q, 0.1=8.2 Hz, 4H), 1.72-1.60 (m, 5H); $^{13}$C NMR (CDCl$_3$) δ 138.19, 138.17, 138.0, 137.9, 115.0, 114.9, 114.77, 114.75, 106.9, 105.3, 104.2, 103.8, 67.6, 67.5, 67.3, 67.1, 63.7, 60.3, 45.7, 42.6, 34.3, 31.9, 30.34, 30.29, 30.27, 30.24, 28.88, 28.86, 28.82, 28.7; IR (film) 2938, 1640, 1443, 1356, 1227, 1095, 1023, 968, 909, 774 cm$^{-1}$; HRMS (M+Na$^+$) calcd for C$_{15}$H$_{26}$O$_4$Na 293.1723. found 293.1722. (4_fraction2): yield 52% (14.9 mg); $^1$H NMR (CDCl$_3$) δ 5.89-5.75 (m, 2H), 5.24-5.13 (m, 1H), 5.12-4.89 (m, 5H), 3.84-3.68 (m, 2H), 3.69-3.54 (m, 2H), 3.49-3.34 (m, 2H), 2.67-2.47 (m, 1H), 2.22-2.00 (m, 5H), 1.89-1.78 (m, 1H), 1.75-1.62 (m, 4H); $^{13}$C NMR (CDCl$_3$) δ 138.31, 138.29, 138.24, 138.0, 114.9, 114.69, 114.66, 114.63, 107.3, 105.3, 104.9, 104.7, 67.9, 67.6, 67.27, 67.17, 63.6, 60.7, 46.7, 44.5, 34.4, 32.2, 30.42, 30.35, 28.9, 28.8, 28.7; IR (film) 2937, 1640, 1445, 1362, 1230, 1091, 1044, 965, 909, 876 cm$^{-1}$; FIRMS (M+Na$^+$) calcd for C$_{15}$H$_{26}$O$_4$Na 293.1723. found 293.1731.

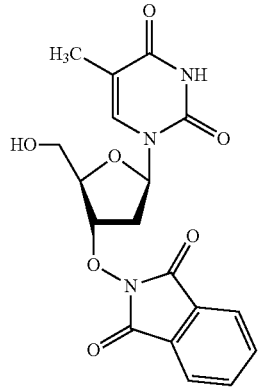

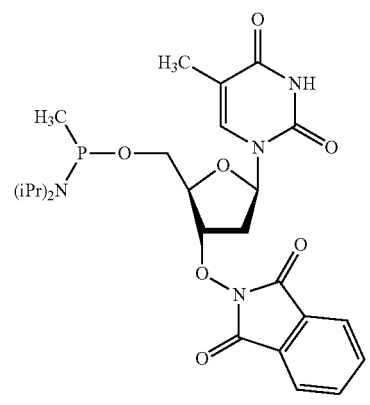

Preparation of 5.

To a solution of 9 (0.50 g, 1.3 mmol) in DCM (30 mL, the solubility in DCM is very poor) was added DIPEA (450 μL, 2.6 mmol). The mixture was cooled to 0° C. and N,N-diisopropylamino methyl phosphonamidic chloride (0.36 mg, 2.0 mmol) was added dropwise. The mixture was allowed to warm to 25° C. and stirred for 4 h. The solution becomes clear when the reaction is complete. The DCM layer was washed with NaHCO$_3$ solution and then with brine. The organic phase was dried over NaSO$_4$. The solvent was evaporated under vacuum and the residue was purified by column chromatography using a mixture of DCM and EtOAc (1:1) with 1% Et$_3$N, yielding 0.41 g (60%) of 5 as white crystals. $^1$H NMR (acetone-d$_6$) δ 10.02 (br s, 1H), 7.89 (m, 4H), 7.68, 7.56 (each s, 1H), 6.52 (m, 1H), 5.08 (m, 1H), 4.51 (m, 1H), 3.85 (m, 2H), 3.62 (m, 1H), 3.53 (m, 2H), 2.71 (dd, 1 H, J=14.7, 5.6 Hz), 2.37 (m, 1H), 1.86 (dd, 3 H, J=3.9, 1.1 Hz), 1.17 (m, 9H), 1.08 (t, 6 H, J=7.1 Hz); $^{13}$C NMR (CDCl$_3$) δ 205.2, 205.0, 163.6, 163.3, 150.3, 135.4, 135.3, 134.79, 134.77, 129.17, 129.15, 123.3, 110.1, 88.62, 88.55, 84.8, 84.5, 82.83, 82.76, 82.72, 82.66, 67.2, 66.5, 44.2, 44.0, 43.9, 36.5, 36.4, 25.3, 24.1, 23.5, 17.1, 17.0, 16.9, 11.73, 11.68; $^{31}$P NMR (CDCl$_3$) δ 125.25, 123.41. IR (film) 2966, 1753, 1681, 1466, 1363, 1277, 1184, 1123, 1062, 970, 876, 701 cm$^{-1}$; HRMS (M+H$^+$) calcd for C$_{25}$H$_{34}$N$_4$O$_7$P 533.2165. found 533.2155.

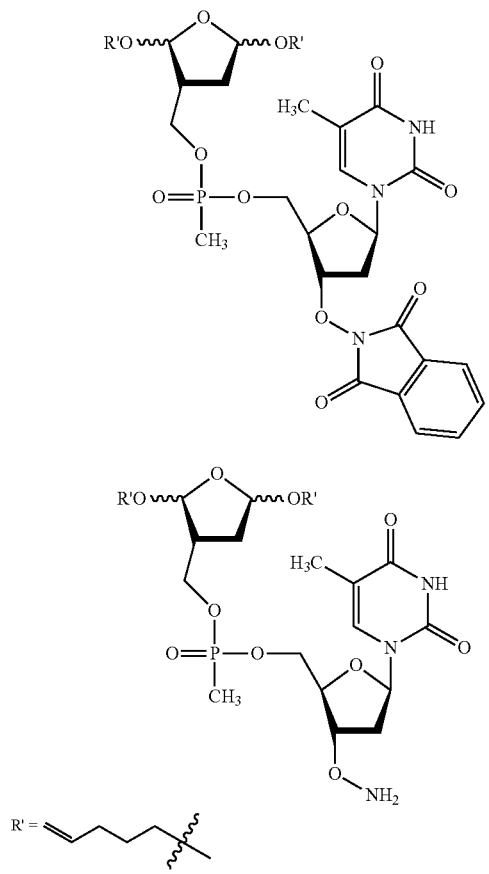

Preparation of 7.

To a solution of 5 (112 mg, 0.21 mmol) and 4 (54 mg, 0.2 mmol) in MeCN (500 µL) was added 5-ethylthio-1H-tetrazole (1.0 mL, 0.25 mmol, 0.25 M solution in MeCN) via syringe under argon and the resulting mixture was stirred for 2 h, at which time t-BuOOH in decane (0.2 mL, 5 M solution) was added and the solution was stirred for an additional 30 min. The solvent was evaporated under vacuum and the residue was loaded on silica gel column. Elution with DCM containing 3% MeOH gave 68 mg (63%) of the phthalimide nucleotide (6) as a white foam. $^1$H NMR (CDCl$_3$) δ 8.70 (s, 1H), 7.85-7.79 (m, 4H), 7.43, 7.40, 7.38, 7.35 (each s, 1H), 6.44 (t, J=7.0 Hz, 1H), 5.89-5.72 (m, 2H), 5.22-5.11 (m, 1H), 5.08-4.89 (m, 6H), 4.56 (m, 1H), 4.42-4.19 (m, 2H), 4.12-3.86 (m, 2H), 3.81-3.63 (m, 2H), 3.46-3.30 (m, 2H), 2.86-2.73 (m, 1H), 2.72-2.61 (m, 1H), 2.33-2.19 (m, 1H), 2.17-2.03 (m, 5H), 1.93, 1.92 (each d, J=1.2 Hz, 3H), 1.89-1.74 (m, 1H), 1.73-1.61 (m, 4H), 1.58-1.44 (m, 3H); $^{13}$C NMR (CDCl$_3$) δ 163.74, 163.72, 163.4, 150.0, 149.9, 138.24, 138.19, 135.6, 135.5, 134.92, 134.91, 128.7, 123.9, 114.73, 114.68, 111.43, 111.37, 106.4, 106.3, 104.50, 104.48, 87.49, 87.48, 85.8, 85.7, 81.4, 81.3, 81.2, 68.1, 67.68, 67.67, 67.65, 67.34, 67.33, 66.0, 65.9, 64.9, 45.3, 45.22, 45.20, 36.6, 36.5, 34.28, 34.25, 30.32, 30.30, 30.27, 28.9, 28.79, 28.77, 12.5, 12.4, 11.8, 11.6, 10.3, 10.2; $^{31}$P NMR (CDCl$_3$) δ 31.98, 31.62, 31.28; IR (film) 2929, 1735, 1688, 1467, 1370, 1312, 1277, 1249, 1187, 1106, 977, 913, 877, 702 cm$^{-1}$; FAB-HRMS (M+Na$^+$) calcd for C$_{34}$H$_{44}$N$_3$O$_{12}$NaP 740.2555. found 740.2569.

To a solution of 6 (68 mg, 0.095 mmol) in THF (1 mL) was added a solution of hydrazine in water (0.2 mL, 6 wt %). After stirring the solution at 25° C. for 5 min, the solvents were evaporated under vacuum and the residue was purified by column chromatography using DCM with 5% methanol. This afforded 44 mg (81%) of 7 as a white foam. $^1$H NMR (CDCl$_3$) δ 8.82 (s, 1H), 7.48, 7.45, 7.44, 7.43 (each d, J=1.2 Hz, 1H), 6.33-6.24 (m, 1H), 5.80 (m, 2H), 5.49 (s, 2H), 5.21-5.11 (m, 1H), 5.05-4.91 (m, 5H), 4.37-4.25 (m, 3H), 4.25-4.14 (m, 1H), 4.13-3.91 (m, 2H), 3.77-3.66 (m, 2H), 3.45-3.33 (m, 2H), 2.72-2.62 (m, 1H), 2.54-2.45 (m, 1H), 2.16-2.05 (m, 5H), 1.96 (m, 1H), 1.94, 1.93 (each d, J=1.2 Hz, 3H), 1.86-1.76 (m, 1H), 1.71-1.60 (m, 4H), 1.57-1.47 (m, 3H); $^{13}$C NMR (CDCl$_3$) δ 163.5, 150.3, 150.2, 138.23, 138.18, 138.17, 135.2, 135.1, 134.3, 123.5, 114.75, 114.69, 111.39, 111.38, 106.5, 106.3, 105.1, 104.49, 104.48, 102.3, 100.0, 85.1, 83.4, 83.3, 81.83, 81.77, 68.1, 67.71, 67.68, 67.4, 67.3, 65.91, 65.85, 65.8, 45.30, 45.26, 45.2, 36.80, 36.75, 34.4, 34.3, 30.32, 30.30, 28.79, 28.77, 12.53, 12.47, 11.9, 11.8, 10.4, 10.3; $^{31}$P NMR (CDCl$_3$) δ 31.99, 31.56, 31.19; IR (film) 2925, 1696, 1466, 1416, 1365, 1233, 1097, 988, 910, 820, 713 cm$^{-1}$; FAB-HRMS (M+Na$^+$) calcd for C$_{26}$H$_{42}$N$_3$O$_{10}$NaP 610.2500. found 610.2491.

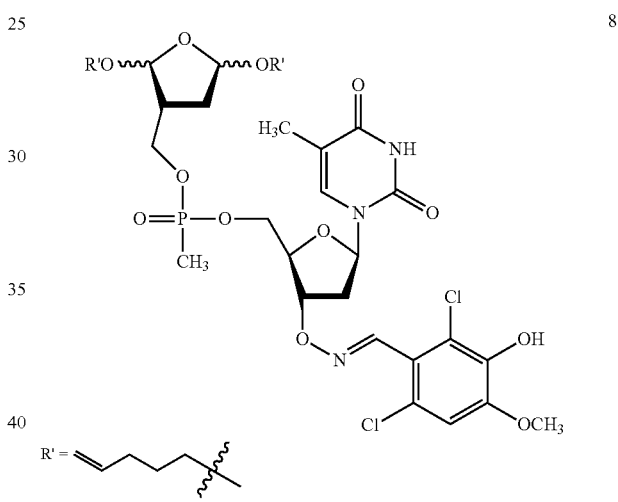

Preparation of 8.

Alkoxyamine 7 (22 mg, 0.037 mmol) was added to a solution of 2,6-dichloro-3-hydroxy-4-methoxy benzaldehyde (10 mg, 0.043 mmol) and acetic acid (10 mg, 10 µL, 0.16 mmol) in DMSO (300 µL). The resulting mixture was incubated at 37° C. for 5 h. DMSO was evaporated under high vacuum and the residue was purified by column chromatography using 3% methanol solution in DCM, affording 20.8 mg of 8 (79%) as a colorless oil. $^1$H NMR (CDCl$_3$) δ 8.99, 8.97, 8.95 (each s, 1H), 8.32 (s, 1H), 7.52, 7.50, 7.48, 7.46 (each d, J=1.2 Hz, 1H), 6.87 (s, 1H), 6.46 (m, 1H), 6.32 (m, 1H), 5.85-5.74 (m, 2H), 5.13 (m, 1H), 5.02-4.92 (m, 6H), 4.43-4.01 (m, 5H), 3.93 (s, 3H), 3.70 (m, 2H), 3.39 (m, 2H), 2.68 (m, 2H), 2.25-2.04 (m, 6H), 1.95, 1.94 (each d, J=1.2 Hz, 3H), 1.86-1.74 (m, 2H), 1.71-1.60 (m, 4H), 1.59-1.49 (m, 3H); $^{13}$C NMR (CDCl$_3$) δ 163.5, 150.4, 148.1, 146.7, 141.8, 138.3, 138.19, 138.18, 135.2, 135.1, 125.4, 120.7, 120.2, 114.72, 114.71, 114.67, 114.66, 111.5, 111.3, 106.5, 106.4, 105.1, 104.50, 104.49, 85.3, 85.2, 82.5, 68.1, 67.70, 67.68, 67.4, 67.3, 56.6, 56.4, 45.3, 37.4, 37.3, 34.3, 30.32, 30.30, 28.80, 28.77, 12.54, 12.48, 10.44; $^{31}$P NMR (CDCl$_3$) δ 31.98, 31.52, 31.19; IR (film) 2940, 1690, 1599, 1491, 1275, 1245, 1061, 1008, 968, 915, 833, 767 cm$^{-1}$; HRMS (M+Na$^+$) calcd for C$_{34}$H$_{46}$N$_3$O$_{12}$NaPCl$_2$ 812.2088. found 812.2111; $\epsilon$268=24, 240 cm$^{-1}$M$^{-1}$ in MeCN.

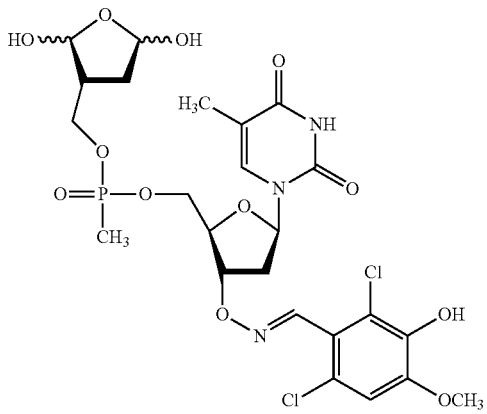

1a

Preparation of 1a.

To a solution of 8 (23 mg, 0.029 mmol) in MeCN (with 1% water) (0.5 mL) was added solution of NBS (12.9 mg, 0.073 mmol) in MeCN (0.1 mL) at −5° C. The reaction mixture was stirred for 3 min, at which time it was quenched with 0.1 mL of a saturated solution of Na$_2$S$_2$O$_3$ and NaHCO$_3$. The organic layer was separated and the solvent was evaporated under reduced pressure at RT. The residue was redissolved in 100 μL MeCN/water mixture (1:4) and loaded on C18 silica gel column, made from a Pasteur pipette (1.5 g silica). The product was eluted using a mixture of MeCN and water: 3×1 mL of 20% MeCN; 3×1 mL of 30% MeCN; 3×1 mL of 50% (Total: 9 fractions 1 mL each). Two main components were isolated as a mixture (fraction 8), representing the cyclic and the dialdehyde forms −10.5 mg (56%). $^1$HNMR (CD$_3$CN) δ 8.28 (s, 1H), 7.45 (s, 1H), 7.00 (s, 1H), 6.31-6.21 (m, 1H), 5.50-4.84 (m, 3H), 4.40-4.31 (m, 1H), 4.27-4.18 (m, 2H), 4.10-3.90 (m, 2H), 3.82 (s, 3H), 3.75-3.52 (m, 2H), 3.48-3.25 (m, 2H), 2.62-2.44 (m, 1H), 2.37-2.16 (m, 2H), 1.81 (m, 4H), 1.63-1.37 (m, 6H); $^{31}$P NMR (CD$_3$CN) 32.08, 32.05, 32.00, 31.93, 31.90, 31.87, 31.83, 31.81, 31.74, 31.62, 31.59, 31.55, 31.52, 31.48, 31.45, 31.44, 31.42, 31.35, 31.31, 22.81; HRMS (M+H$^+$) calcd for C$_{24}$H$_{29}$Cl$_2$N$_3$O$_{11}$P 636.0917. found 636.0931; am =20,000 cm$^{-1}$M$^{-1}$ in 50% MeCN in water.

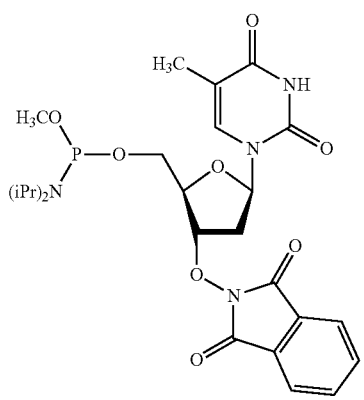

S2

Preparation of the Methoxy Phosphoramidite of 9 (S2).

To a solution of alcohol 9 (200 mg, 0.50 mmol) and DIPEA (260 mg, 2.00 mmol) in DCM (5 mL) was added N,N-diisopropylamino methoxy phosphonamidic chloride (157 mg, 0.80 mmol) at 0° C. The resulting solution was stirred at 25° C. for 1 h. The solvent was evaporated and the residue was purified by column chromatography using a gradient 10%-20% EtOAc in DCM with 1% of Et3N, yielding 160 mg (60%) of S2. $^1$H NMR (CD3CN) δ 9.20 (s, 1H), 7.84 (m, 4H), 7.63, 7.55 (each m, 1H), 6.42 (td, 8.5, 5.6 Hz, 1H), 4.99 (m, 1H), 4.45 (m, 1H), 3.77 (m, 2H), 3.49 (m, 2H), 3.37, 3.33 (each d, J=13.4 Hz, 3H), 2.62, 2.59 (each d, J=6.2, 1H), 2.27 (m, 1H), 1.85, 1.84 (each d, J=0.5 Hz, 3H), 1.13 (m, 12H); $^{13}$C NMR (CD$_3$CN) δ 164.0, 163.6, 150.52, 150.46, 135.7, 135.5, 134.8, 129.1, 123.3, 117.3, 110.5, 88.4, 88.3, 84.6, 84.4, 82.29, 82.26, 82.20, 82.16, 63.8, 63.7, 62.9, 62.7, 50.2, 50.1, 49.9, 49.1, 44.95, 44.89, 42.66, 42.54, 36.3, 36.0, 24.04, 24.02, 24.01, 23.97, 23.95, 23.94, 23.90, 22.28, 22.26, 22.05, 22.04, 20.1, 11.6; $^{31}$P NMR (CD$_3$CN) δ 149.46, 149.23; IR (film) 2967, 1735, 1682, 1465, 1364, 1184, 970, 876, 700 cm$^{-1}$; MALDI-TOF MS (M+Na$^+$) calcd for C$_{25}$H$_{33}$N$_4$NaO$_8$P 571.2. found 571.2.

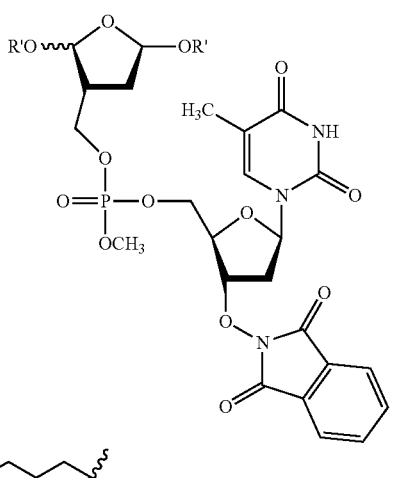

S3

Coupling of Methoxy Phosphoramidite with 4 (S3).

The above methoxy phosphoramidite (S2, 52 mg, 0.10 mmol) and 4 (27 mg, 0.10 mmol) were dissolved in anhydrous MeCN (0.5 mL). 5-Ethylthio-1H-tetrazole (0.50 mL, 0.13 mmol, 0.25 M solution in MeCN) was added to the reaction mixture via syringe under argon and the resulting solution was stirred for an hour at RT. t-BuOOH in decane (0.10 mL, 5 M solution) was added to the reaction mixture and stirred for additional 20 min. The solvents were evaporated under vacuum and the residue was purified by column chromatography using DCM with 3% MeOH, yielding 60 mg (82%) of S3. $^1$H NMR (CDCl$_3$) δ 9.13 (d, J=4.7 Hz, 1H), 7.83, 7.77 (each m, 4H), 7.37 (m, 1H), 6.47 (m, 1H), 5.78 (m, 2H), 5.12 (m, 1H), 4.96 (m, 6H), 4.54 (s, 1H), 4.31 (m, 2H), 4.02

(m, 2H), 3.76 (m, 3H), 3.68 (m, 2H), 3.37 (m, 2H), 2.76 (ddd, J=14.4, 5.8, 1.8 Hz, 1H), 2.66 (m, 1H), 2.24 (m, 1H), 2.07 (m, 6H), 1.90 (s, 3H), 1.81 (m, 1H), 1.64 (m, 4H); $^{13}$C NMR (CDCl$_3$) δ 163.74, 163.73, 163.68, 150.2, 138.22, 138.21, 138.17, 138.15, 135.4, 134.9, 128.7, 123.9, 114.71, 114.69, 114.67, 114.60, 111.49, 111.44, 107.2, 106.2, 106.1, 105.1, 104.8, 104.5, 87.6, 87.5, 85.37, 85.31, 81.1, 81.0, 68.0, 67.68, 67.67, 67.65, 67.34, 67.25, 63.4, 54.70, 54.69, 49.9, 46.7, 45.20, 45.18, 45.14, 45.11, 36.6, 34.16, 34.10, 30.34, 30.30, 30.27, 28.84, 28.81, 28.76, 22.93, 22.91, 12.42, 12.40; $^{31}$P NMR (CDCl$_3$) δ 0.07, 0.02, −0.00, −0.03, −0.09; IR (film) 2937, 1735, 1690, 1467, 1369, 1276, 1017, 877, 703 cm$^{-1}$; HRMS (M+Na$^+$) calcd for C$_{34}$H$_{44}$N$_3$NaO$_{13}$P 756.2509. found 756.2496.

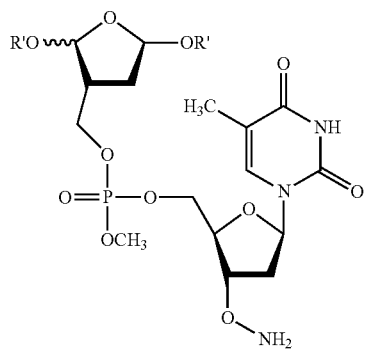

S4

Preparation of the Alkoxyamine S4.

To a solution of S3 (60 mg, 0.08 mmol) in THF (0.5 mL) was added hydrazine (0.05 mL, 6% solution in water) and the mixture was stirred for 5 min at 25° C. The volatile components were evaporated under vacuum and the residue was purified by column chromatography using DCM with 4.5% MeOH, yielding 38 mg (77%) of S4. $^1$H NMR (CDCl$_3$) δ 9.14 (s, 1H), 7.43 (m, 1H), 6.31 (m, 1H), 5.80 (m, 2H), 5.48 (s, 2H), 5.13 (m, 1H), 4.98 (m, 5H), 4.36 (m, 1H), 4.28 (m, 3H), 4.05 (m, 2H), 3.80, 3.79 (each d, J=11.2 Hz, 3H), 3.69 (m, 2H), 3.37 (m, 2H), 2.68 (m, 1H), 2.47 (ddd, J=14.0, 5.7, 1.6 Hz, 1H), 2.08 (m, 5H), 1.98 (m, 1H), 1.92 (t, J=1.4 Hz, 3H), 1.81 (m, 1H), 1.65 (m, 4H); $^{13}$C NMR (CDCl$_3$) δ 163.7, 150.45, 150.43, 138.21, 138.16, 138.15, 135.2, 134.2, 123.5, 114.74, 114.73, 114.72, 114.69, 111.5, 111.4, 106.27, 106.24, 106.20, 105.1, 104.5, 84.9, 83.42, 83.40, 83.38, 81.62, 81.54, 68.10, 68.04, 68.0, 67.71, 67.69, 67.4, 54.62, 54.60, 54.56, 54.55, 45.21, 45.14, 36.72, 36.68, 34.21, 34.20, 34.18, 30.31, 30.30, 30.28, 28.77, 28.75, 12.44, 12.43; $^{31}$P NMR (CDCl$_3$) δ 0.37, 0.35, 0.31, 0.28, 0.19, 0.17, 0.15, 0.13; IR (film) 2937, 1691, 1467, 1274, 1032, 857 cm$^{-1}$; HRMS (M+Na$^+$) calcd for C$_{26}$H$_{42}$N$_3$NaO$_{11}$P 626.2455. found 626.2460.

S5

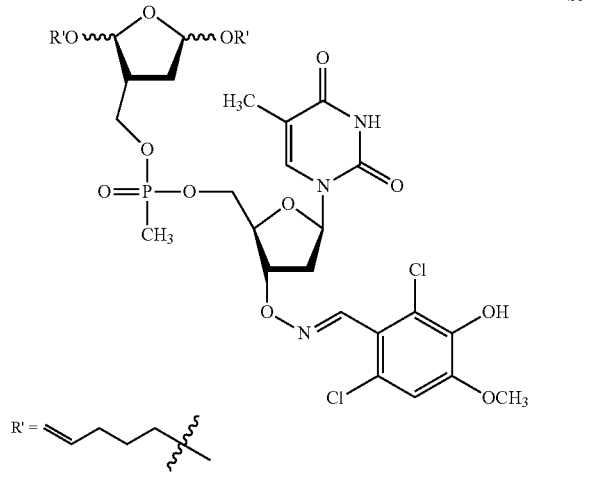

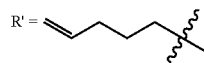

Preparation of the Oxime of the Methyl Phosphate Triester (S5).

A solution of S4 (32 mg, 0.05 mmol), 2,6-dichloro-3-hydroxy-4-methoxybenzaldehyde (15.5 mg, 0.07 mmol) and AcOH (9 mg, 0.15 mmol) in DMSO (0.5 mL) was incubated at 37° C. overnight. The DMSO was evaporated under vacuum and the residue was purified by column chromatography using DCM with 3% MeOH, yielding 36 mg (84%) of the oxime as a foam. $^1$H NMR (CDCl$_3$) δ 9.17 (s, 1H), 8.31 (s, 1H), 7.48 (m, 1H), 6.86 (s, 1H), 6.50 (m, 1H), 6.40 (s, 1H), 5.80 (m, 2H), 5.13 (dt, J=5.3, 2.5 Hz, 1H), 4.98 (m, 6H), 4.42 (m, 1H), 4.32 (m, 2H), 4.06 (m, 2H), 3.92 (s, 3H), 3.81 (m, 3H), 3.71 (m, 2H), 3.38 (m, 2H), 2.62 (m, 2H), 2.18 (m, 1H), 2.09 (q, J=6.9 Hz, 5H), 1.95 (s, 3H), 1.80 (m, 1H), 1.65 (p, J=7.6 Hz, 4H); $^{13}$C NMR (CDCl$_3$) δ 163.6, 150.5, 148.2, 146.8, 141.8, 138.24, 138.17, 135.2, 125.4, 120.6, 120.2, 114.72, 114.67, 111.71, 111.66, 111.3, 106.24, 106.21, 104.5, 102.3, 85.0, 82.5, 82.2, 82.1, 67.7, 67.4, 66.9, 56.6, 54.65, 54.60, 45.22, 45.15, 37.3, 34.18, 34.15, 30.31, 30.30, 30.29, 28.85, 28.77, 28.76, 12.5; $^{-1}$) NMR (CDCl$_3$) δ 0.28, 0.26, 0.09, 0.04; IR (film) 2941, 1690, 1439, 1275, 1017, 953 cm$^{-1}$; HRMS (M+Na$^+$) calcd for C$_{34}$H$_{46}$Cl$_2$N$_3$NaO$_{13}$P 828.2043. found 828.2044.

2a

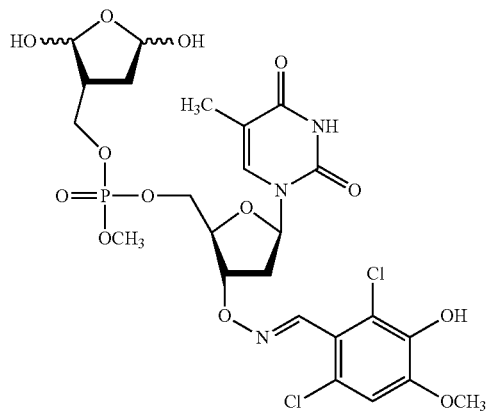

Preparation of 2a.

To a solution of S5 (10 mg, 0.012 mmol) in MeCN (0.5 mL) with 1% water was added NBS (6 mg, 0.035 mmol) in MeCN (0.06 mL) at 0° C. The solution was stirred for 5 min before it was quenched with 1:1 mixture of saturated solutions of Na$_2$S$_2$O$_3$ and NaHCO$_3$ (0.03 mL). The organic layer was separated and the solvent was evaporated under vacuum. The residue was redissolved in a mixture of water and MeCN (1:1) (0.04 mL) and then diluted with water (0.06 mL) before it was loaded on the column (the solution becomes cloudy after the dilution because of poor solubility of the product). The product was purified on a column made of a Pasteur pipette (with 1 g of C18 silica) using a gradient 20%-50% MeCN in water (collected about 12 fractions 1 mL each). The fractions containing the desired product were combined and lyophilized, yielding 5.5 mg (66%) of 2a as a white powder. $^1$H NMR (CD$_3$CN) δ 8.31 (s, 1H), 7.45 (s, 1H), 7.03 (s, 1H), 6.29 (m, 1H), 5.46-5.16 (m, 2H), 4.94 (m, 1H), 4.36 (m, 1H), 4.29 (m, 2H), 4.03 (m, 2H), 3.87 (s, 3H), 3.75 (m, 3H), 2.52 (m, 2H), 2.31 (m, 2H), 1.84 (m, 4H); $^{31}$P NMR (CD$_3$CN) δ −0.16, −0.25; MALDI-TOF MS (dialdehyde form M+Na$^+$) calcd for C$_{24}$H$_{28}$Cl$_2$N$_3$NaO$_{12}$P 674.068. found 673.759.

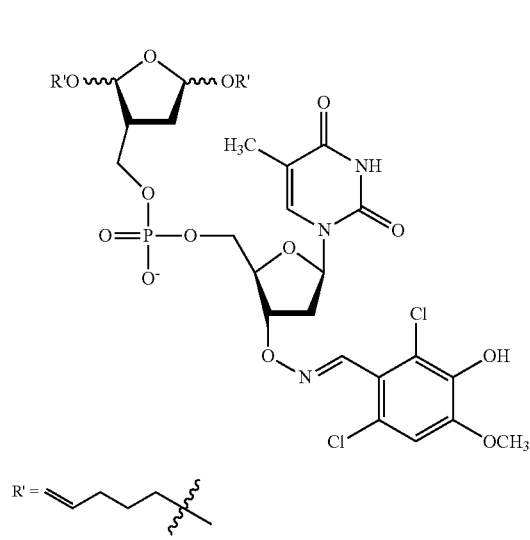

R' = [alkenyl group]

Preparation of S6.

To a solution of S5 (95 mg, 0.12 mmol) in DMF (0.5 mL) was added disodium 2-carbamoyl-2-cyanoethylene-1,1-dithiolate (See: Söderbück, E. Acta. Chem. Scand. 1970, 24, 228-234 for preparation of the reagent.) (61.9 mg, 0.24 mmol) in DMF (0.5 mL) and the mixture was incubated at 25° C. for 1 h. DMF was evaporated under vacuum and the residue was purified by C18 silica using a gradient 20%-50% MeCN in water. The fractions containing the desired product were lyophilized yielding 94 mg (99%) of S6 as white powder. The sodium salt was converted to TBA (tetrabutylammonium) salt using Dowex 50WX8-400 cation exchange resin. A Pasteur pipette was loaded with 1 mL of slurry (1.7 meq/mL) and washed with a solution of TBA-OH until protons are fully exchanged by TBA (pH of the collected solution becomes basic). The column is washed with distilled water several times (to wash out the excess TBA-OH). The solution of compound in water (0.5 mL) was passed through the column very slowly (1 drop per second). The column is washed with 30% MeCN in water until (the TBA salt is very hydrophobic and is not fully soluble in water) all the material comes out. The solutions were combined and lyophilized yielding 113 mg (93%) of S6 as a white powder. $^1$H NMR (MeOH-d$_4$) δ 8.32 (s, 1H), 7.90 (d, J=1.2 Hz, 1H), 7.02 (s, 1H), 6.46 (m, 1H), 5.81 (m, 2H), 5.12 (m, 1H), 5.06 (d, J=6.3 Hz, 1H), 5.02 (m, 2H), 4.98 (m, 1H), 4.92 (m, 2H), 4.41 (m, 1H), 4.14 (m, 2H), 3.91 (s, 3H), 3.84 (m, 2H), 3.67 (m, 2H), 3.35 (m, 2H), 3.23 (m, 8H), 2.56 (m, 2H), 2.43 (m, 1H), 2.08 (m, 5H), 1.96 (s, 3H), 1.90 (m, 1H), 1.65 (m, 12H), 1.41 (h, J=7.4 Hz, 8H), 1.02 (t, J=7.4 Hz, 12H); $^{13}$C NMR (MeOH-d$_4$) δ 165.0, 149.2, 146.31, 146.29, 142.8, 138.15, 138.13, 136.6, 123.9, 120.7, 120.5, 113.7, 111.2, 110.8, 106.69, 106.65, 104.81, 104.78, 84.9, 83.8, 83.4, 83.3, 67.21, 67.19, 66.97, 66.95, 65.61, 65.56, 65.27, 65.21, 65.17, 58.12, 58.09, 58.06, 55.7, 45.45, 45.37, 36.8, 33.75, 33.67, 30.1, 28.74, 28.71, 23.4, 19.34, 19.33, 19.31, 12.58, 12.57, 11.4; $^{31}$P NMR (MeOH-d$_4$) δ 0.08, 0.03, −0.03, −0.04; IR (film) 2936, 1688, 1466, 1238, 1056, 957, 831, 732; HRMS (M−) calcd for C$_{33}$H$_{43}$Cl$_2$N$_3$O$_{13}$P 790.1916. found 790.1904.

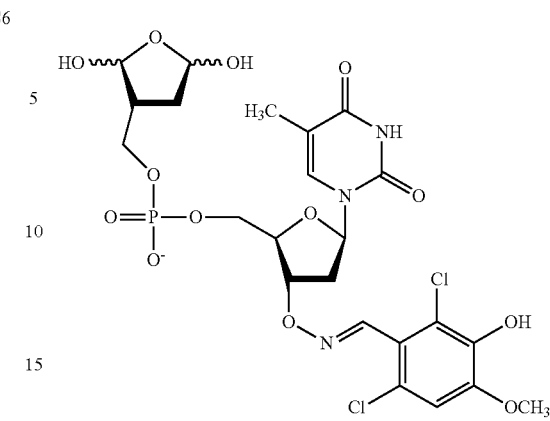

Preparation of 3a.

To a solution of S6 (6 mg, 0.006 mmol) in MeCN (0.6 mL) with 3% water and phosphate solid buffer pH 7 (20 mg) was added NBS (3.2 mg, 0.018 mmol) in MeCN (0.05 mL) under vigorous stirring at 0° C. The stirring was continued for 5 min and a 1:1 mixture of saturated solutions of Na$_2$S$_2$O$_3$ and NaHCO$_3$ (0.1 mL) was added. The reaction flask was connected to vacuum and MeCN was evaporated. The residue (water and salts) was diluted with water and purified by C18 silica (1 g) on a column made of a Pasteur pipette using a gradient 5%-20% MeCN in water (collected about 12 fractions 1 mL each). The fractions were combined and lyophilized yielding 1.4 mg (33%) of 3a as white powder. $^1$H NMR (D2O) δ 8.30 (s, 1H), 7.89 (s, 1H), 6.99 (s, 1H), 6.45 (m, 1H), 5.62-5.33 (m, 2H), 5.06 (m, 2H), 4.49 (m, 2H), 4.15 (m, 1H), 4.07 (m, 2H), 3.87 (s, 3H), 2.62 (m, 2H), 2.46 (m, 2H), 1.91 (m, 4H); $^{31}$P NMR (162 MHz, D2O) δ 2.16, −0.07, −0.12; MALDI-TOF MS (dialdehyde form M+Na$^+$) calcd for C$_{23}$H$_{26}$Cl$_2$N$_3$NaO$_{12}$P 660.053. found 660.010.

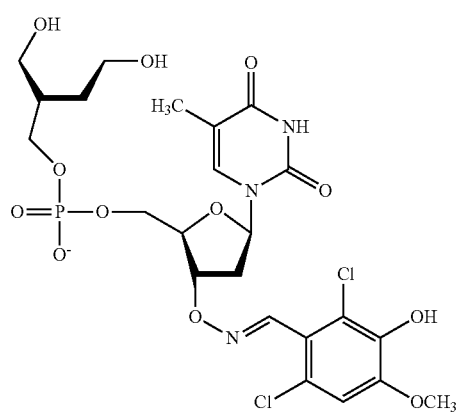

Preparation of 17.

A solution of 3a (20 μL, 5 mM) in water was reduced with NaBH$_4$ (2 μL, 100 mM). The excess reducing agent was quenched with AcOH after 5 min. TLC analysis of the product (eluted with 40% MeCN in water on C18 silica plates) shows a similar R$_f$ with the starting material. MALDI-TOF MS (diol form M+Na$^+$) calcd for C$_{23}$H$_{30}$Cl$_2$N$_3$NaO$_{12}$P 664.084. found 660.043.

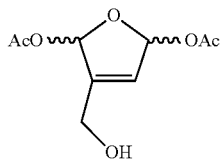

S7

Preparation of S7.

To a suspension of Pb(OAc)$_4$ (2 g, 4.5 mmol) in glacial AcOH (10 mL) was added 3-hydroxymethylfuran (400 mg, 4.1 mmol) and the mixture was stirred at 25° C. for 20 h (the solution becomes clear). AcOH was evaporated and Et$_2$O was added to the residue. The precipitate was filtered, the filtrate was collected, evaporated and the residue was purified by column chromatography using DCM with 30% EtOAc, yielding 600 mg (68%) of S7 as a mixture of 2 major isomers (ratio 2:1, according to $^1$H NMR). $^1$H NMR (CDCl$_3$) δ 6.94 (m, 1H), 6.74 (m, 1H), 6.09 (m, 1H), 4.33 (m, 2H), 2.13, 2.10 (each d, J=12.8 Hz, 6H); $^{13}$C NMR (CDCl$_3$) δ 170.35, 170.34, 170.0, 169.9, 145.5, 145.3, 125.0, 124.7, 101.3, 100.6, 99.99, 99.91, 99.4, 57.6, 57.5, 21.16, 21.14, 21.05; IR (film) 1737, 1374, 1222, 1178, 967 cm$^{-1}$; HRMS (M+NH4$^+$) calcd for C$_9$H$_{16}$NO$_6$ 234.0972. found 234.0980.

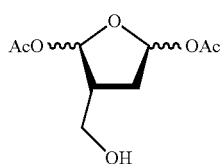

20

Preparation of 20.

A solution of S7 (600 mg, 2.7 mmol) in EtOAc (60 mL) was placed in a hydrogenation apparatus. 5% Rhodium on alumina (300 mg) was added and the hydrogenation was carried out at 70 psi for 14 h. The solution was filtered off through alumina and the EtOAc was evaporated in vacuo. The residue was purified by silica gel chromatography using DCM with 50% EtOAc to elute the first diastereomer 20a (90 mg), followed by 60% EtOAc to elute the second component 20b, which represent a mixture of several diastereomers, but the major one represent about 90% (170 mg) of the mixture. Total amount of isolated material represented 260 mg (44%). 20a: $^1$H NMR (CDCl$_3$) δ 6.41 (dd, J=5.9, 1.2 Hz, 1H), 6.33 (s, 1H), 3.81 (m, 1H), 3.67 (m, 1H), 2.49 (m, 2H), 2.04 (d, J=1.9 Hz, 6H), 1.85 (m, 1H); $^{13}$C NMR (CDCl$_3$) δ 170.0, 169.7, 100.6, 98.5, 62.6, 45.9, 31.9, 21.18, 21.17; IR (film) 1737, 1365, 1225, 1093, 964 cm$^{-1}$; HRMS (M+NH4$^+$) calcd for C$_9$H$_{18}$NO$_6$ 236.1129. found 236.1134. 20b: $^1$H NMR (CDCl$_3$) δ 6.31 (m, 2H), 3.68 (m, 2H), 2.63 (m, 1H), 2.41 (m, 1H), 2.10 (m, 6H), 1.84 (m, 1H); $^{13}$C NMR (CDCl$_3$) 170.5, 170.1, 99.08, 99.06, 99.03, 98.7, 98.2, 71.5, 71.0, 68.5, 64.5, 64.2, 60.8, 60.4, 48.1, 46.8, 45.4, 39.8, 39.1, 35.1, 34.8, 31.8, 25.2, 21.4, 21.21, 21.17; IR (film) 1737, 1371, 1227, 1102, 958 cm$^{-1}$; HRMS (M+NH4$^+$) calcd for C$_9$H$_{18}$NO$_6$ 236.1129. found 236.1128.

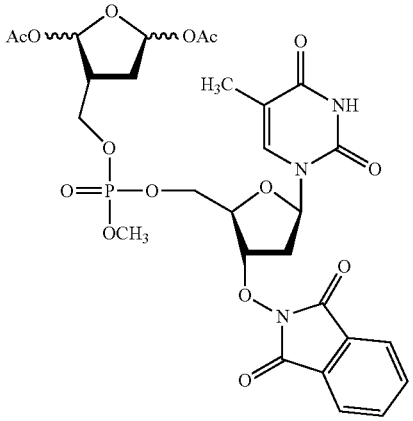

S8

Preparation of S8.

To a solution of 20b (170 mg, 0.33 mmol) and S2 (60 mg, 0.27 mmol) in anhydrous MeCN (2 mL) was added a solution of 5-ethylthio-1H-tetrazole in MeCN (1.32 mL, 0.33 mmol, 0.25 M solution). The resulting mixture was stirred for 1 h at 25° C. at which time t-BuOOH in decane (0.20 mL, 5 M solution) was added and the mixture was stirred for an additional 20 min. The solvents were evaporated under vacuum and the residue was purified by column chromatography using DCM with 3% MeOH, yielding 160 mg (87%) of S8 as a mixture of 4 diastereomers, according to the $^{31}$P NMR spectrum. $^1$H NMR (CDCl$_3$) δ 9.34 (s, 1H), 7.79 (m, 4H), 7.36 (s, 1H), 6.44 (m, 1H), 6.38 (m, 1H), 6.33 (m, 1H), 5.00 (m, 1H), 4.54 (s, 1H), 4.33 (m, 2H), 4.14 (m, 2H), 3.77 (ddd, J=11.5, 6.2, 5.5 Hz, 3H), 2.75 (m, 1H), 2.64 (m, 1H), 2.49 (m, 1H), 2.31 (m, 1H), 2.03 (m, 3H), 1.98 (m, 3H), 1.88 (m, 3H), 1.81 (m, 1H); $^{13}$C NMR (CDCl$_3$) δ 169.53, 169.51, 169.50, 169.47, 169.43, 163.86, 163.84, 163.76, 163.74, 150.23, 150.20, 135.8, 134.9, 128.7, 123.9, 111.43, 111.39, 111.37, 111.28, 99.30, 99.25, 99.22, 98.12, 98.10, 98.05, 87.4, 85.6, 81.1, 81.0, 67.3, 66.9, 54.90, 54.87, 54.84, 54.81, 54.79, 54.76, 44.15, 44.13, 44.11, 44.08, 44.06, 44.04, 36.56, 36.48, 36.43, 36.39, 31.60, 31.58, 31.56, 31.54, 27.0, 21.16, 21.14, 21.04, 21.02, 21.01, 14.9, 12.4; $^{31}$P NMR (CDCl$_3$) δ −0.15, −0.31, −0.43, −0.53; IR (film) 2345, 1731, 1687, 1467, 1367, 1227, 1016, 970, 877, 731, 701 cm-1; HRMS (M+Na$^+$) calcd for C$_{28}$H$_{32}$N$_3$NaO$_{15}$P 704.1469. found 704.1463.

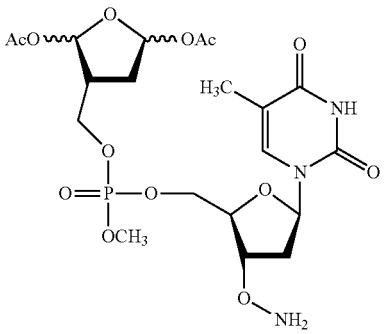

21

Preparation of 21.

The above phthalimide, S8 (160 mg, 0.23 mmol) in THF (3 mL) was treated with hydrazine (0.2 mL, 6% solution in water) for 10 min. TLC analysis shows complete reaction.

The volatile components were evaporated under vacuum and the residue was purified by column chromatography using DCM with 4.5% MeOH, yielding 60 mg (48%) of free 21 as a mixture of 4 diastereomers according to the $^{31}$P NMR spectrum. $^1$H NMR (CDCl$_3$) δ 9.28 (s, 1H), 7.42 (s, 1H), 6.41 (m, 1H), 6.36 (m, 1H), 6.29 (m, 1H), 5.60 (s, 2H), 4.35 (m, 1H), 4.28 (m, 3H), 4.14 (m, 2H), 3.80 (ddd, J=11.2, 4.6, 2.8 Hz, 3H), 2.65 (m, 1H), 2.51 (m, 2H), 2.04 (m, 6H), 1.98 (m, 1H), 1.92 (m, 3H), 1.81 (m, 1H); $^{13}$C NMR (CDCl$_3$) δ 169.50, 169.48, 169.47, 169.45, 169.44, 169.43, 169.42, 163.81, 163.80, 150.47, 150.45, 135.36, 135.34, 135.33, 134.3, 123.4, 111.44, 111.42, 111.40, 111.32, 99.23, 99.21, 99.19, 99.17, 98.09, 98.08, 98.06, 98.05, 85.03, 84.98, 84.96, 83.36, 83.34, 83.28, 81.62, 81.60, 81.58, 81.52, 68.23, 68.22, 68.18, 68.17, 68.16, 66.88, 66.87, 66.84, 66.83, 66.81, 66.79, 54.78, 54.75, 54.72, 54.70, 54.69, 54.65, 44.15, 44.13, 44.11, 44.08, 44.06, 44.05, 44.01, 36.63, 36.58, 31.62, 31.59, 31.57, 21.16, 21.14, 21.08, 21.07, 12.40, 12.39; $^{31}$P NMR (CDCl$_3$) δ 0.14, −0.05, −0.12, −0.18; IR (film) 2345, 1745, 1688, 1470, 1367, 1227, 1099, 1004, 968, 906 cm$^{-1}$; HRMS (M+Na$^+$) calcd for C$_{20}$H$_{30}$N$_3$NaO$_{13}$P 574.1414. found 574.1424.

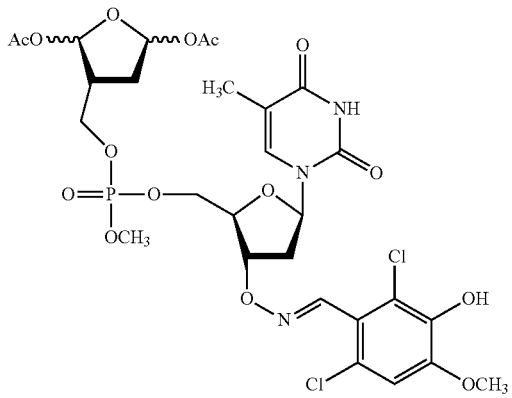

S9

Preparation of S9.

A solution of 21 (30 mg, 0.05 mmol), 2,6-dichloro-3-hydroxy-4-methoxybenzaldehyde (15 mg, 0.07 mmol) and AcOH (9 mg, 0.15 mmol) in DMSO (0.5 mL) was incubated at 37° C. overnight. The DMSO was evaporated under vacuum and the residue was purified by column chromatography using DCM with 3% MeOH, yielding 45 mg (100%) of the oxime as a foam. $^1$H NMR (CDCl$_3$) 9.46 (s, 1H), 8.28 (s, 1H), 7.44 (s, 1H), 6.83 (s, 1H), 6.44 (m, 1H), 6.39 (m, 1H), 6.33 (m, 1H), 4.94 (m, 1H), 4.40 (m, 1H), 4.33 (m, 2H), 4.15 (m, 2H), 3.89 (s, 3H), 3.79 (ddd, J=11.2, 3.9, 1.7 Hz, 3H), 2.64 (m, 1H), 2.49 (m, 1H), 2.17 (m, 1H), 2.00 (m, 6H), 1.91 (s, 3H), 1.80 (m, 1H); $^{13}$C NMR (CDCl$_3$) δ 169.42, 169.39, 163.81, 163.80, 150.55, 150.54, 148.4, 146.8, 142.1, 135.3, 125.1, 120.5, 120.4, 111.54, 111.53, 111.51, 111.45, 111.3, 99.22, 99.19, 99.16, 98.04, 98.00, 85.0, 82.3, 82.1, 67.9, 66.8, 56.6, 54.79, 54.76, 54.73, 54.70, 54.67, 44.13, 44.06, 40.8, 37.19, 37.14, 31.60, 31.58, 31.56, 21.15, 21.14, 21.13, 21.05, 21.04, 12.4; $^{31}$P NMR (CDCl$_3$) δ 0.01, −0.10, −0.20, −0.28; IR (film) 2957, 1749, 1690, 1275, 1228, 1017, 970, 862 cm$^{-1}$; HRMS (M+Na$^+$) calcd for C$_{28}$H$_{34}$Cl$_2$N$_3$NaO$_{15}$P 776.1002. found 776.0981.

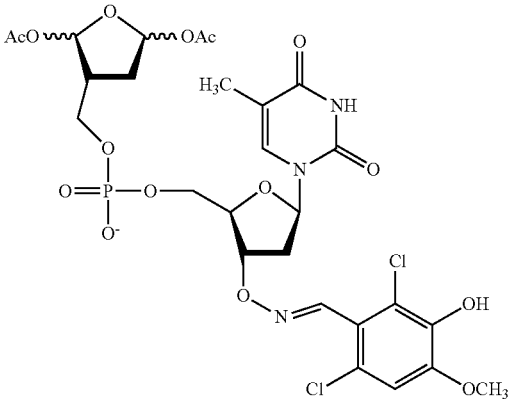

18

Preparation of 18.

To a solution of the above oxime (45 mg, 0.06 mmol) in DMF (0.2 mL) was added disodium 2-carbamoyl-2-cyanoethylene-1,1-dithiolate (31.2 mg, 0.12 mmol) in DMF (0.2 mL) and the mixture was incubated at 25° C. for 1 h. DMF was evaporated under vacuum and the residue was purified by C18 silica using a gradient 10%-40% MeCN in water. The fractions containing the desired product were lyophilized yielding 32 mg (78%) of sodium salt 18 as white powder. $^1$HNMR (D2O) δ 8.11 (s, 1H), 7.72 (s, 1H), 6.76 (s, 1H), 6.35 (m, 1H), 6.25 (d, J=5.3 Hz, 1H), 6.21 (d, J=8.5 Hz, 1H), 5.00 (m, 1H), 4.41 (s, 1H), 4.13 (m, 2H), 3.97 (m, 2H), 3.81 (s, 3H), 2.65 (q, J=8.5 Hz, 1H), 2.56 (m, 1H), 2.49 (p, J=8.2, 7.2 Hz, 1H), 2.35 (dt, J=14.9, 7.5 Hz, 1H), 2.03 (m, 6H), 1.90 (m, 1H), 1.86 (s, 3H); $^{13}$C NMR (D$_2$O) δ 172.60, 172.56, 172.49, 166.10, 166.08, 151.1, 149.2, 142.5, 137.1, 123.9, 120.0, 119.2, 111.21, 111.20, 100.1, 98.9, 83.1, 56.2, 30.8, 20.55, 20.45, 11.7; $^{31}$P NMR (D$_2$O) δ −0.28, −0.29; HRMS (M-) calcd for C$_{27}$H$_{31}$Cl$_2$N$_3$O$_{15}$P 738.0875. found 738.0874; ε270 nm=18800 cm$^{-1}$M$^{-1}$ in water.

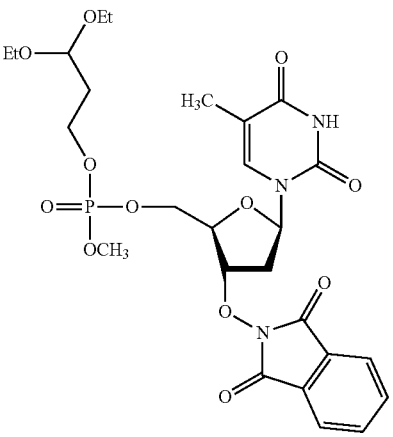

S10

Preparation of S10.

To a solution of S2 (52 mg, 0.1 mmol) and 3,3-diethoxy-1-propanol (19 mg, 0.13 mmol) in anhydrous MeCN (0.5 mL) was added a solution of 5-ethylthio-1H-tetrazole in MeCN (0.5 mL, 0.13 mmol, 0.25 M solution) and the resulting mixture was stirred for 1 h at 25° C. t-BuOOH in decane (0.10 mL, 5 M solution) was added to the reaction mixture and stirring was continued for an additional 20 min. The solvents were evaporated under vacuum and the residue was purified by column chromatography using DCM with 3.5% MeOH, yielding 40 mg (65%) of S10 as a mixture of 2 diastereomers, according to the $^{31}$P NMR spectrum. $^1$H NMR (CDCl$_3$) δ 9.04 (s, 1H), 7.83, 7.78 (each m, 4H), 7.41 (s, 1H), 6.50 (m, 1H), 4.98 (d, J=6.3 Hz, 1H), 4.61 (q, J=5.7 Hz, 1H), 4.55 (m, 1H), 4.31 (m, 2H), 4.14 (q, J=6.6 Hz, 2H), 3.78, 3.77 (each d, J=11.2 Hz, 3H), 3.60 (m, 2H), 3.46 (m, 2H), 2.76 (ddd, J=14.6, 5.8, 1.9 Hz, 1H), 2.24 (m, 1H), 1.97 (dt, J=11.3, 5.8 Hz, 2H), 1.91 (s, 3H), 1.45 (d, J=6.3 Hz, 2H), 1.17 (m, 6H); $^{13}$C NMR (CDCl$_3$) δ 163.74, 163.68, 150.16, 150.14, 135.46, 135.43, 134.9, 128.7, 123.9, 111.50, 111.47, 102.6, 99.52, 99.47, 87.63, 87.61, 85.2, 81.19, 81.10, 67.1, 64.98, 64.93, 64.87, 61.86, 61.72, 61.68, 61.59, 59.2, 54.62, 54.58, 54.57, 54.52, 47.4, 36.71, 36.68, 35.8, 34.68, 34.64, 34.61, 34.58, 22.9, 19.3, 15.32, 15.28, 15.27, 12.4; $^{31}$P NMR (CDCl$_3$) δ 0.04, −0.01; IR (film) 2973, 1736, 1690, 1467, 1373, 1277, 1187, 1126, 1033, 877, 703 cm$^{-1}$; HRMS (M+Na$^+$) calcd for C$_{26}$H$_{34}$N$_3$NaO$_{12}$P 634.1778. found 634.1752.

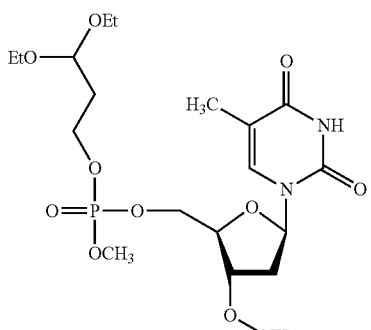

S11

Preparation of S11.

Phthalimide S10 (35 mg, 0.06 mmol) in THF (0.5 mL) reacted with hydrazine (0.1 mL, 6% solution in water) for 5 min at 25° C. The volatile components were evaporated and the residue was purified by column chromatography using DCM with 5% MeOH, yielding 24 mg (89%) of S11 as an oil. $^1$H NMR (CDCl$_3$) δ 9.02 (s, 1H), 7.46 (m, 1H), 6.32 (ddd, J=8.9, 5.6, 3.4 Hz, 1H), 5.50 (s, 2H), 4.63 (q, J=5.6 Hz, 1H), 4.37 (d, J=6.3 Hz, 1H), 4.30 (m, 3H), 4.16 (m, 2H), 3.81, 3.80 (each d, J=11.2 Hz, 3H), 3.64 (m, 2H), 3.49 (m, 2H), 2.48 (dd, J=14.4, 6.0 Hz, 1H), 2.00 (m, 3H), 1.93 (t, J=1.2 Hz, 3H), 1.90 (s, 1H), 1.19 (m, 6H); $^{13}$C NMR (CDCl$_3$) δ 163.7, 150.42, 150.40, 135.3, 111.49, 111.44, 99.53, 99.50, 84.94, 84.91, 83.53, 83.49, 81.68, 81.60, 67.9, 64.84, 64.79, 64.73, 61.72, 61.67, 61.58, 54.52, 54.49, 54.47, 54.43, 36.80, 36.74, 34.71, 34.64, 15.30, 15.28, 12.40; $^{31}$P NMR (CDCl$_3$) δ 0.39, 0.28; IR (film) 2972, 1691, 1467, 1274, 1033, 857 cm-1; HRMS (M+Na$^+$) calcd for C$_{18}$H$_{32}$N$_3$NaO$_{10}$P 504.1723. found 504.1724.

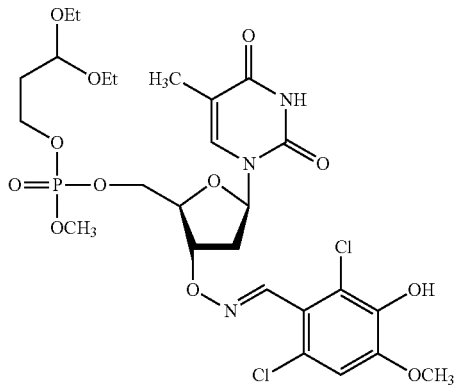

S12

Preparation of S12.

A solution of S11 (28 mg, 0.06 mmol), 2,6-dichloro-3-hydroxy-4-methoxybenzaldehyde (17 mg, 0.08 mmol) and AcOH (9 mg, 0.15 mmol) in DMSO (0.5 mL) was incubated at 37° C. overnight. The DMSO was evaporated under vacuum and the residue was purified by column chromatography using DCM with 4% MeOH, yielding 40 mg (97%) of S12 as a foam. 1H NMR (CDCl$_3$) δ 9.26 (s, 1H), 8.31 (s, 1H), 7.51 (m, 1H), 6.85 (s, 1H), 6.51 (m, 1H), 6.48 (m, 1H), 4.97 (d, J=7.0 Hz, 1H), 4.62 (td, J=5.7, 3.6 Hz, 1H), 4.42 (m, 1H), 4.33 (m, 2H), 4.17 (q, J=6.7 Hz, 2H), 3.91 (s, 3H), 3.80 (d, J=11.2 Hz, 3H), 3.63 (m, 2H), 3.48 (m, 2H), 2.63 (dd, J=14.1, 5.9 Hz, 1H), 2.16 (m, 1H), 1.99 (q, J=6.4 Hz, 2H), 1.95 (s, 3H), 1.17 (m, 6H); $^{13}$C NMR (CDCl$_3$) δ 163.7, 150.61, 150.60, 148.2, 146.8, 141.9, 135.3, 125.4, 120.6, 120.2, 111.69, 111.64, 111.3, 99.55, 99.52, 85.00, 84.99, 82.6, 82.27, 82.21, 64.89, 64.84, 64.78, 61.75, 61.73, 61.61, 56.6, 54.57, 54.53, 54.51, 54.47, 37.46, 37.40, 34.71, 34.69, 34.65, 34.63, 15.3, 12.4; $^{31}$P NMR (CDCl$_3$) δ 0.30, 0.17; IR (film) 2973, 1690, 1492, 1440, 1274, 1032, 860 cm$^{-1}$; HRMS (M+Na$^+$) calcd for C$_{26}$H$_{36}$Cl$_2$N$_3$NaO$_{12}$P 706.1311. found 706.1289.

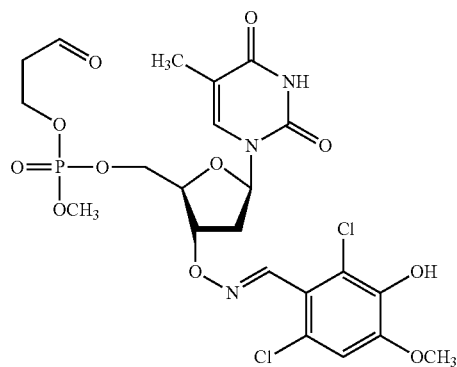

16

Preparation of 16.

A solution of S12 (40 mg, 0.06 mmol) was refluxed in acetone (1 mL) in presence of pyridinium p-toluenesulfonate (10 mg, 0.04 mmol) and water (0.05 mL) for 5 h. TLC analysis shows insignificant amount of starting material. The solvents were evaporated and the residue was purified by column chromatography on silica using DCM with 5% MeOH, yielding 26 mg (76%) of 16 as a white solid. $^1$H NMR (CD3CN) δ 9.68 (m, 1H), 9.28 (s, 1H), 8.29 (s, 1H), 7.46 (s, 1H), 7.03 (s, 1H), 6.32 (m, 1H), 5.45 (s, 1H), 4.97 (m, 1H), 4.34 (m, 3H), 4.27 (m, 2H), 3.89 (s, 3H), 3.73 (d, J=11.2 Hz, 3H), 2.79 (td, J=5.9, 1.3 Hz, 2H), 2.53 (dd, J=14.0, 5.7 Hz, 1H), 2.28 (dt, J=15.6, 8.4 Hz, 1H), 1.85 (d, J=1.1 Hz, 3H); $^{13}$C NMR (CD$_3$CN) δ 200.10, 200.08, 163.7, 150.5, 148.9, 146.7, 142.4, 135.55, 135.53, 124.4, 120.5, 119.9, 111.8, 110.7, 84.91, 84.87, 82.46, 82.44, 82.1, 82.0, 67.4, 61.67, 61.66, 61.62, 61.61, 56.4, 54.34, 54.33, 54.31, 54.27, 54.25, 43.55, 43.48, 36.45, 36.44, 11.5; $^{31}$P NMR (CD3CN) δ −0.17, −0.28; IR (film) 2956, 1680, 1487, 1439, 1263, 1032, 841, 731 cm$^{-1}$; HRMS (M+Na$^+$) calcd for C$_{22}$H$_{27}$Cl$_2$N$_3$O$_{11}$P 610.0760. found 610.0765.

Synthesis of Oxime Library.

The oxime library was prepared and stored in 96 well PCR plates. A solution of alkoxyamine 7 in DMSO (1.16 mL, 17.4 mM) was aliquoted into 232 wells (5 µL in each, 87 nmol). Solutions of each aldehyde (232) in DMSO (150 mM) were added to each well (0.7 µL, 105 nmol), followed by the addition of a solution of acetic acid in DMSO (1 µL, 300 nmol). The plates were sealed and incubated at 37° C. for 12 h. DMSO and acetic acid were evaporated by placing the plates in a desiccator under high vacuum for 5 h. The contents of each well were redissolved in 22 µL of DMSO to provide a 4 mM solution of oxime and stored at −20° C.

Screening of Inhibitor Library a. Deprotection.

To screen the library, 5 µL of DMSO solutions of 8 were transferred to another set of plates and placed under vacuum to remove DMSO. The contents of each well were redissolved in 5 µL of acetonitrile containing 12 mM of N-bromosuccinimide. After 20 min incubation at 0° C., 1 µL of $Na_2S_2O_3$ solution in water (100 mM) and additional 4 µL of acetonitrile were added.

B. Pol β Inhibition.

A solution of Pol β (10 nM) in 50 mM HEPES buffer pH=7.5, 5 mM $MgCl_2$, 0.2 mM EDTA, 50 mM KCl and 0.01% Tween 20, was added to a 96 well format microtiter plate (360 µL in each well). It is worth noting that the well should be full to obtain accurate fluorescence data (approximately 380 µL). The solutions of inhibitors in acetonitrile produced above (10 µL) were transferred to the plates containing Pol β and incubated for 20 min (final concentration of the inhibitor was approximately 50 µM). To determine the polymerase activity in the presence of each inhibitor, a solution of 13 (3.8 µL, 5 µM) and dTTP (3.8 µL, 10 mM) were also added (to make final [13]=50 nM and 100 µM of dTTP). The plates were immediately placed in the microtiter plate reader and the measurements were recorded.

Inhibition of Pol β Studied by Fluorescence as a Function of Concentration of Specific Inhibitors.

Solution of Pol β (360 µL, 10 nM) in 50 mM HEPES buffer pH=7.5, 5 mM $MgCl_2$, 0.2 mM EDTA, 50 mM KCl and 0.01% Tween 20, was added to the wells of a 96 well format microtiter plate. It is worth noting that the well should be full in order to get accurate fluorescence data (approximately 380 µL). The solutions of inhibitors (40×) in acetonitrile obtained after pentenyl deprotection (10 µL) were transferred to the wells containing Pol β and incubated for 20 min. To determine the polymerase activity of enzyme in the presence of each inhibitor, solutions of ternary complex 13 (3.8 µL, 5 µM) and dTTP (3.8 µL, 10 mM) were also added (to make final 50 nM of 13 and 100 µM of dTTP). The plates were placed immediately in the microtiter plate reader Cary Eclipse Varian and the measurements started.

Time Dependent Inhibition of Pol β Via Fluorescence Spectroscopy.

Pol β (360 µL, 10 nM) in 50 mM HEPES buffer pH=7.5, 5 mM $MgCl_2$, 0.2 mM EDTA, 50 mM KCl and 0.01% Tween 20, was added to 5 wells of a 96 well format microtiter plate. The inhibitor solution (40×, 10 µL) was added to the first well and preincubated for 20 min. At this time, the same portion of inhibitor was added to the second well. Equal amounts of inhibitor were added to subsequent wells after an additional 20, 35, and 40 min. Once the inhibitor was added to the fifth well, solutions of ternary complex 13 (3.8 pit, 5 µM) and dTTP (3.8 µL, 10 mM) were also added and the fluorescence measurement was started immediately. This procedure yielded the activity of Pol β (10 nM) after different preincubation times (0, 5, 20, 40, 60 min) with the inhibitor.

Time Dependent Inactivation of Pol β by 1a (3a) Via Gel Electrophoresis.

A solution ($CH_3CN$) of 1a or 3a (10 µL) was added to Pol β (400 µL, 5 nM) in 50 mM HEPES buffer pH=7.5, 5 mM $MgCl_2$, 0.2 mM EDTA, 50 mM KCl and 0.01% Tween 20. The final inhibitor concentration varied between 5 and 30 µM. At specific times (0-40 min), which represent the preincubation periods, aliquots (25 pit) were mixed with $3'$-$^{32}$P-15 (1 µL, 5 µM). Aliquots (4 µL) of the reactions were removed (5, 10, 15, 20, 30 min) and unreacted dRP was stabilized by reacting with $NaBH_4$ (1 µL, 0.5 M). The aliquots containing reducing agent were kept on ice for 1 h before mixing with loading buffer (5 µL) and analyzing by 20% denaturing PAGE. The preincubation times for each inhibitor concentration varied: 5 µM—0, 10, 20, 30, 40 min; 10, 15 µM—0, 5, 10, 15, 20 min; 20 µM—0, 1, 3, 5, 10 min; 30 µM —0, 1, 2, 3, 5 min.

Dialysis of Pol β-Inhibitor 1a (3a) Reaction.

Pol β (500 nM) was preincubated with the inhibitor 1a or 3a (50 µM) for 30 min in a solution containing 50 mM HEPES buffer pH=7.5, 5 mM $MgCl_2$, 0.2 mM EDTA, 50 mM KCl, 0.01% Tween 20 and 10% glycerol. An aliquot (5 µL) was diluted to 500 pit and placed in a dialysis cassette. A similar dialysis was set up using Pol β that was not reacted with 3a. The experiment was carried out in triplicate. Dialysis was carried out in the reaction buffer. The remaining lyase activity of the enzyme was measured on aliquots (25 µL, 0, 1, 2, 3 days) using $3'$-$^{32}$P-15 (200 nM). Aliquots (4 µL, 5, 10, 15, 20, 30 min) from the reactions were stabilized with $NaBH_4$ solution (1 µL, 0.5 M). The aliquots were kept on ice for 1 h before mixing with loading buffer (5 µL) and analyzing by 20% denaturing PAGE.

IC50 value for inhibitor 3a.

Pol β (500 nM) was preincubated with inhibitor 3a (0, 2.5, 5, 7.5, 10, 20, 30, 40, 50, 70, 100 µM) for 30 min in a solution containing 50 mM HEPES buffer pH=7.5, 5 mM $MgCl_2$, 0.2 mM EDTA, 50 mM KCl and 0.01% Tween 20. Aliquots (1 µL) were diluted to 100 µL. The remaining lyase activity of the enzyme was determined using $3'$-$^{32}$P-15 (200 nM). Aliquots (4 µL) were removed at indicated time points (5, 10, 15, 20, 30 min) and stabilized with $NaBH_4$ solution (1 µL, 0.5 M). The aliquots were kept on ice for 1 h before mixing with loading buffer (5 µL) and analyzing by 20% denaturing PAGE.

Specificity of the Inhibitor 3a for Pol β Against Klenow (Exo-).

A 96 well format microtiter plate was used to probe the polymerase activity of Pol β and Klenow (exo-) in the presence of inhibitor 3a. The plate was charged with the solution containing 13 (50 nM), dTTP (5, 25, 50, 75 µM) and 3a (0, 25, 50 µM) in 50 mM HEPES buffer pH=7.5, 5 mM $MgCl_2$, 0.2 mM EDTA, 50 mM KCl and 0.01% Tween 20. The volume of the solution in each well is approximately 400 µL. Pol β (final concentration, 10 nM) or Klenow exo-(final concentration 5 nM) is added and the measurement of the fluorescence is started immediately.

Assessing the Lyase Activity of DU145 Cell Extracts (Lysates) in the Presence of an Inhibitor.

DU145 cell extract (2.94 mg/mL of protein, 10×10$^6$ cells/mL) was diluted 1:6 with HM buffer (3.5 µL diluted with 20.5 µL of buffer). Solutions of 3a or 18 (all 25× in water, 1 µL, 0, 10, 20, 50, 100 µM) were preincubated with the diluted cell extract for 1 h. The dRP substrate, $3'$-$^{32}$P-15 (1 µL, 25×) was added to obtain 200 nM desired concentration and aliquots (4 µL) were collected at specific time points and stabilized with $NaBH_4$ (1 µL, 1 M). The aliquots were kept on ice for 1 h before mixing with loading buffer (5 μL). The samples were analyzed by 20% denaturing PAGE and quantified using a phosphorimager.

Assessing the Effect of 18 on Lyase Activity of Mouse Embryonic Fibroblast Lysates.

Cell lysate (32 μg protein) from the corresponding cell line (obtained from Dr. Sam Wilson, NIEHS) was incubated in HM buffer with or without 18 (50 μM) for 40 min at 25° C. (10 μL total volume), at which time 3'-$^{32}$P-15 (2 μL, final concentration: 100 nM) was added. Aliquots (4 μL) were removed at 5, 15, and 25 min and frozen in dry-ice, except for Pol λ wild type lysates, from which aliquots were removed at 2, 5, and 10 min. When the reactions were complete, NaBH$_4$ (1 μL, 0.5 M) was added to each aliquot. The aliquots were kept on ice for 1 h before mixing with loading buffer (5 μL). The samples were analyzed by 20% denaturing PAGE and quantified using a phosphorimager.

Preparation of Cell Lysates.

Cells were harvested by mild trypsinzation. The cells were then washed three times with phosphate buffered saline. Cell pellets were suspended in 1× Passive Lysis Buffer (PBL, Promega Corporation, E1941, Madison, Wis.) at concentration of 1×10$^7$ cells per mL and frozen in aliquots at −80° C. Protein concentrations were determined by Bio-Rad protein assay dye (Bio-Rad, 500-0006, Hercules, Calif.) according to the manufacturer's protocol and using bovine serum albumin as a standard.

Cell Culture and Clonogenic Survival.

DU 145 cells were obtained from the American Type Culture Collection (ATCC, HTB-81, Manassas, Va.) and maintained in RPMI 1640 culture medium (Sigma-Aldrich R8758, St. Louis, Mo.), supplemented with 10% fetal bovine serum (Sigma-Aldrich F6178, St. Louis, Mo.). Cultures were grown at 37° C. in a humidified atmosphere of 5% carbon dioxide without any antibiotics and subcultured when they reached confluence. For clonogenic survival analysis, the appropriate number of cells were grown in standard 6-well tissue culture dishes in the growth media (2 mL per well). After 2 days, the cells were treated with Pol β inhibitors (3a or 18) by addition of sterile stock solution in water directly to the growth media to the desired final concentrations. Cells were treated similarly with methyl methanesulfonate (MMS, Sigma-Aldrich, St. Louis, Mo.). For combined treatments, 18 was added to the cells first followed by MMS. The compounds remained present throughout the entire assay. Two weeks after the treatment, the cells were fixed and stained with 0.2% solution of crystal violet in 50% methanol. Colonies with ≥50 cells were then counted. All treatments were carried out in triplicate.

Example 2

Design and Synthesis of Small Molecule DOB Mimics as Potential Irreversible Inhibitors of Pol β

A library of nucleotide inhibitors containing the 1,4-dicarbonyl group that is present in the DOB and pC4-AP lesions that irreversibly inhibit DNA polymerase β was conceived (Scheme 4). A thymidine nucleotide was incorporated to make the molecule DNA-like. Initially, the phosphate diester in DNA was replaced by a more lipophilic methyl phosphonate (1). The molecules contained a carbon between the ring containing the 1,4-dicarbonyl and the methyl phosphonate to improve their chemical stability in aqueous solution by preventing elimination. Finally, structural diversity was introduced in the form of an oxime linkage at the 3'-terminus. The oxime group has proven to be a useful means for introducing structural diversity (represented by "R") into chemical libraries of enzyme inhibitors (Jiang et al., 2005; Chung et al., 2009).

Scheme 4. Representative nucleotide inhibitors containing the 1,4-dicarbonyl group that irreversibly inhibit DNA polymerase β

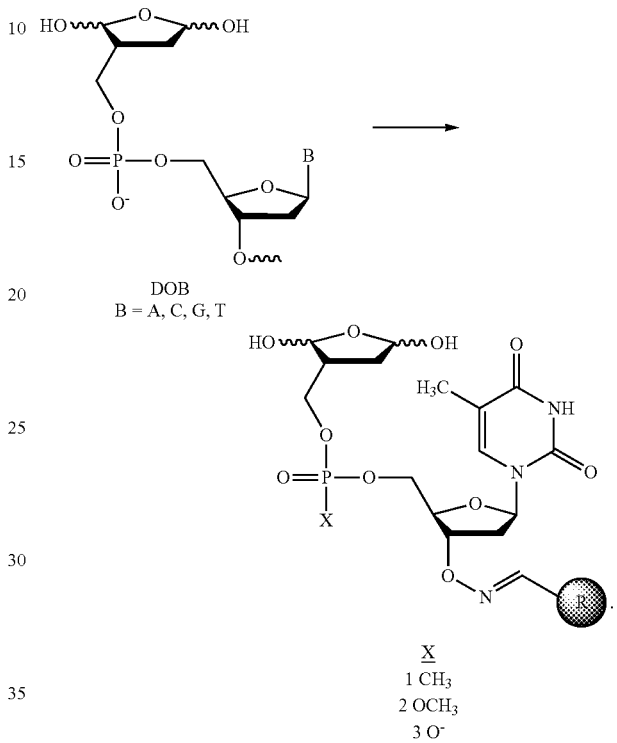

The unmasking of the 1,4-dialdehyde of 1 was anticipated in the final step after the library was prepared containing single compounds in individual wells of microtiter plates (Scheme 5).

Scheme 5.$^a$
Scheme 5. Preparation of nucleotide inhibitor compound (1)

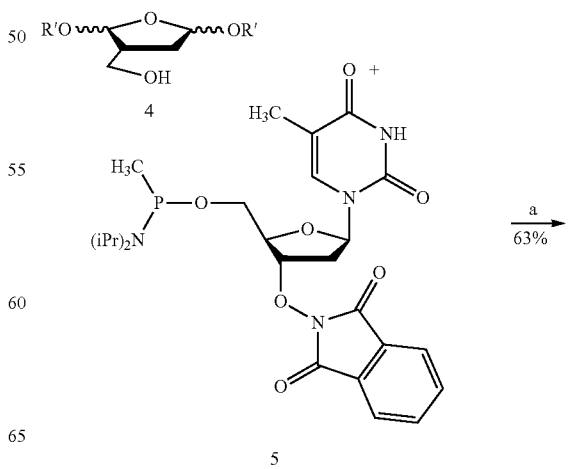

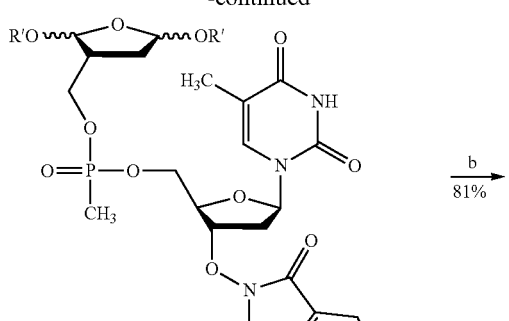

6

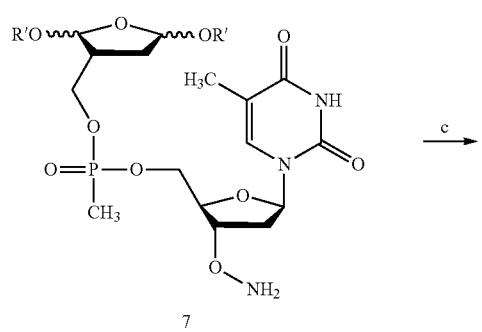

7

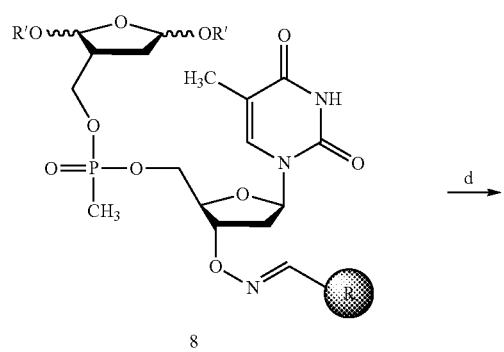

8

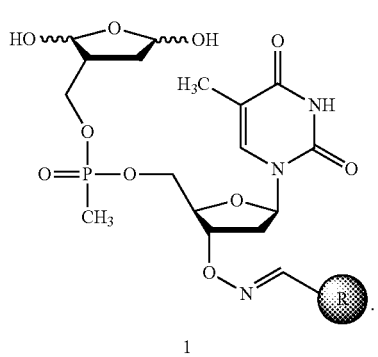

1

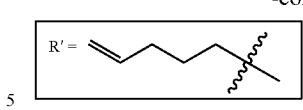

*Key: a) i. tetrazole, CH₃CN, 25° C.
ii. t-BuOOH
b) N₂H₄, THF, 25° C.
c) RCHO, AcOH, DMSO, 37° C.
d) NBS, CH₃CN, -5° C.

The choice of acetal protecting group was important, as it needed to be cleaved rapidly under mild conditions. The pentenyl group was chosen because it had been very useful in carbohydrate synthesis for glycosidic bond formation and is cleaved rapidly under mild oxidizing conditions (Mootoo et al., 1988). The alkoxyamine (7) was the last common intermediate in the library synthesis and was apportioned into the wells of the microtiter plates. The methyl phosphonate coupling to produce 6 was carried out using the phosphonamidite of the thymidine component (5) and the primary alcohol of the protected 1,4-dicarbonyl (4). The coupling yields were higher using this approach due to poor solubility of the corresponding 5'-hydroxy-3'-phthalimide substituted thymidine (9).

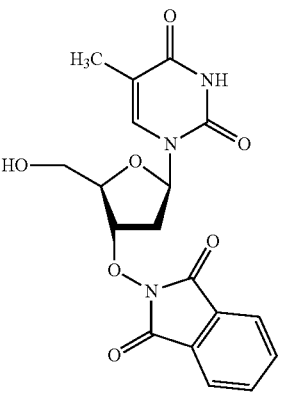

9

Following removal of the phthalimide protecting group using hydrazine, chemical diversity was introduced by reacting 7 separately with one of 232 aldehydes overnight in DMSO and acetic acid. DMSO was removed from the crude mixture of 8 under vacuum prior to deprotecting the bis-acetal with N-bromosuccinimide.

The methyl phosphonamidite (5) was prepared from previously reported 9 under standard phosphitylation conditions in 60% yield (Chen et al., 2010). The requisite hydroxymethyl compound (4) was prepared from 10 using a strategy employed previously for the synthesis of photolabile DOB precursors (Scheme 6) (Kodama and Greenberg, 2005; Bournaud et al., 2010).

Scheme 6. Preparation of compound (4)

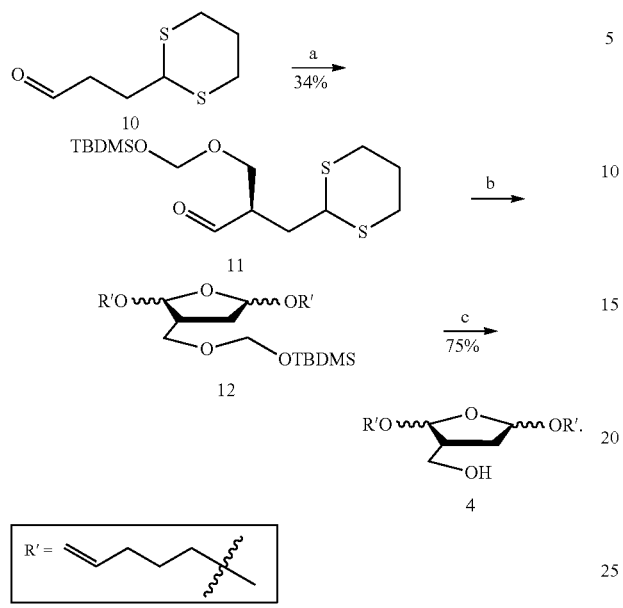

*Key: a) i. CH₂O, prolinol catalyst, toluene, 25° C.
  ii. TBDMSCl
  B) Selectfluor, pent-4-en-1-ol, CH₃CN, 25° C.
  c) TBAF, THF, 0° C.

The hydroxymethyl group was introduced via an aldol condensation with formaldehyde that was ultimately trapped as the silyl ether of the formacetal (11) using a chiral catalyst derived from proline (Boeckman and Miller, 2009). Substituting Selectfluor® for N-bromosuccinimide, which was used in the synthesis of the DOB precursor, to induce cyclization of 11 by oxidatively cleaving the 1,3-dithiane resulted in a significant improvement in yield, albeit as an inseparable mixture of diastereomers of 12 (Liu and Wong, 2002). Two of the 4 diastereomers were separable upon desilylation to 4. Although the stereochemistry of the acetals were unimportant with respect to the properties of the inhibitor candidates, working with less complex mixtures facilitated characterizing subsequent intermediates in the synthetic sequence. A library containing 232 members was synthesized from 4 (Scheme 5) and screened for Pol β inhibition.

Example 3

Screening Inhibitor Candidates Using a Strand Displacement Assay

Inactivation of Pol β's lyase activity by DOB or C4-AP also shuts down the enzyme's ability to extend a primer via strand displacement synthesis (Guan et al., 2010; Jacobs et al., 2011). Consequently, it was speculated that successful small molecules that inactivate the lyase activity would also shut down polymerase activity. This enabled the use of a previously reported fluorescence assay (Scheme 7) in which a ternary substrate (13, 50 nM) containing TAMRA at the 3'-terminus of the displaced strand and quencher (BHQ-2) at the 5'-terminus of the template strand was subjected to Pol β (10 nM) and dTTP (100 μM) (Dorjsuren et al., 2009) Strand displacement synthesis results in fluorescence by TAMRA, and Pol β inhibition is reflected by decreased fluorescence relative to control lacking inhibitor.

Scheme 7. Fluorescence assay in which ternary substrate (13) was subjected to Pol β

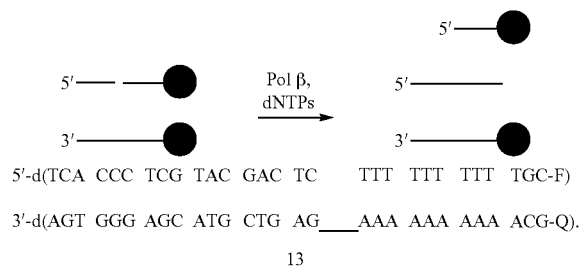

5'-d(TCA CCC TCG TAC GAC TC  TTT TTT TTT TGC-F)

3'-d(AGT GGG AGC ATG CTG AG___AAA AAA AAA ACG-Q).

13

The 232 candidates (FIG. 1) (50 μM) were screened using this method. Several candidates exhibited significant inhibition in the strand displacement assay. Of these, the molecule derived from 2,6-dichloro-3-hydroxy-4-methoxy benzaldehyde (1a) was most effective at reducing fluorescence.

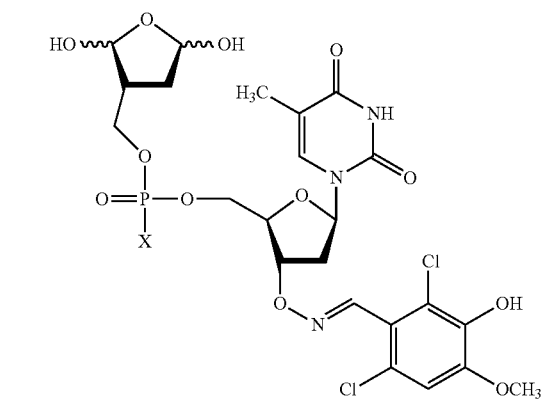

X
1a CH₃
2a OCH₃
3a O⁻

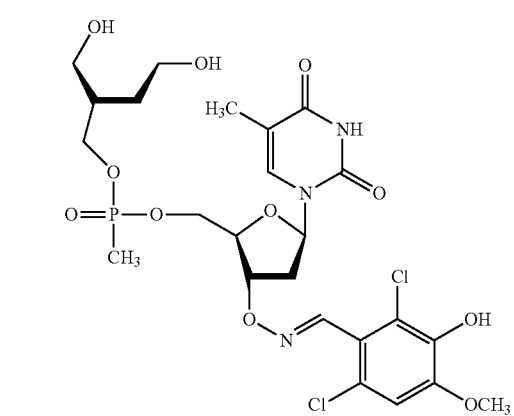

14

Purified 1a significantly inhibited Pol β in the strand displacement assay at as low as 10 μM (FIG. 2A). The reduction product (14) had no effect on enzyme activity (data not shown), indicating that the 1,4-dicarbonyl is required for inhibition. Furthermore, the extent of inhibition was dependent upon the preincubation time (FIG. 2B), a property that is consistent with irreversible inactivation.

Example 4

Direct Examination of Pol β Lyase Inactivation by 1a

The ability of 1a to inhibit Pol β's dRPase activity was examined using 3'-$^{32}$P-15 in which the oligonucleotide containing dRP was labeled.

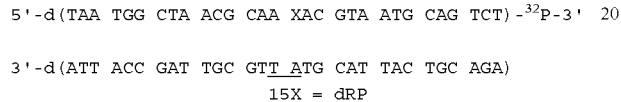

The DNA substrate was added to the reaction following preincubation of 1a with Pol β and subsequent 100-fold dilution. The lyase reaction was monitored by gel electrophoresis. A logarithmic plot of activity in the presence of 1a (up to 30 μM) relative to when no inhibitor is present versus preincubation time decays linearly at each concentration over the range tested (FIG. 3A) (Silverman, 2000). In addition, Pol β activity was not restored following dialysis of the enyzme-inhibitor solution for up to 3 days (FIG. 3B) (Silverman, 2000). Both observations are consistent with irreversible inhibition of Pol β.

Example 5

Effects of Phosphate Backbone Modification on Pol β Inactivation

Using 1a as a lead, the effect of modifying the phosphorous backbone on inhibitor activity was explored by synthesizing the phosphate triester (2a) and phosphate diester (3a) analogues. These candidates were prepared from 4 and 9 via a similar manner as 1a. Phosphate triester 2a exhibited comparable inhibition activity as 1a using the strand displacement assay (Scheme 7) (FIG. 4). This backbone motif was also useful for establishing the necessity of the 1,4-dicarbonyl for irreversible inactivation, as monoaldehdye 16 had no effect on Pol β lyase activity (FIG. 5).

In contrast, introducing the negative charge present in DNA (3a) produced a more potent inhibitor. Direct measurement of Pol β lyase activity showed that 3a was at least 2-fold more potent than 1a and exhibited an IC50 of approximately 16 μM (FIG. 6). Furthermore, as for the methyl phosphonate, dialysis of Pol β incubated with 3a confirmed that inhibition was irreversible, and reduction to the diol (17) provided additional affirmation that the 1,4-dialdehyde was required for inactivation (FIGS. 7 and 8).

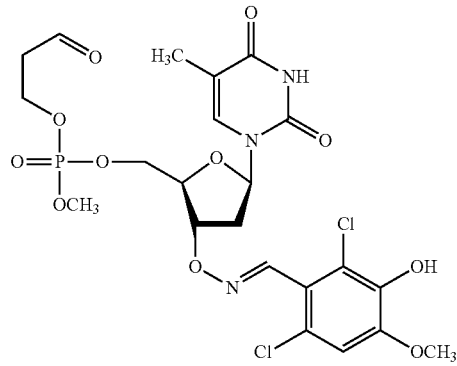

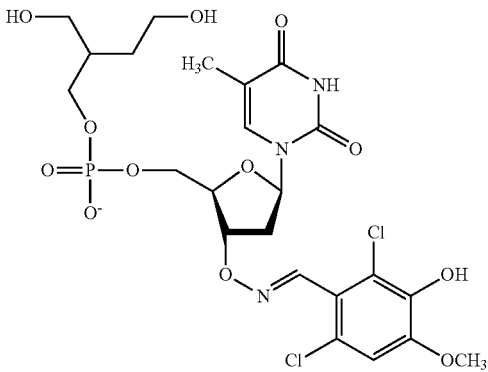

Example 6

Selectivity and Robustness of Pol β Inactivation by Small Molecule DOB Analogues More than one dozen polymerases exist in a human cell. Because there is not access to each of these, the Klenow fragment of DNA polymerase 1 from *E. coli* was used as a primitive test of the inhibitor's (3a) selectivity. While 3a (10 μM) almost completely eliminated Pol β's ability to carry out strand displacement synthesis using 13 (Scheme 7) and dTTP, it had no effect on the Klenow fragment's activity under the same conditions (FIG. 9). However, the efficacy of the 1,4-dicarbonyl containing inhibitor (1a) was compromised by thiols, presumably due to nucleophilic addition (FIG. 10). For instance, preincubation (20 min) of 1a (50 μM) with glutathione (5 mM) resulted in similar Pol β activity as 25 μM inhibitor in the absence of thiol).

Example 7

Design and Synthesis of a Proinhibitor

The adverse effect of glutathione on 1a led to the design of bisacetate 18 as a potential proinhibitor. It was postulated that 18 would be converted into 3a by cellular esterases (Jessen et al., 2008; Ora et al., 2009). Proinhibitor 18 was synthesized from 3-hydroxymethylfuran (19) and 9 (Scheme 8). Following Pb(OAc)$_4$ oxidation and hydrogenation, 18 was coupled with the methyl phosphoramidite obtained from 9. Selective cleavage of the phthalimide group yielded alkoxyamine 21, which was conjugated to 2,6-dichloro-3-hydroxy-4-methoxybenzyaldehyde prior to revealing the phosphate diester (18). As expected, 18 had no effect on Pol (3 lyase activity (data not shown).

Scheme 8. Synthesis of proinhibitor 18

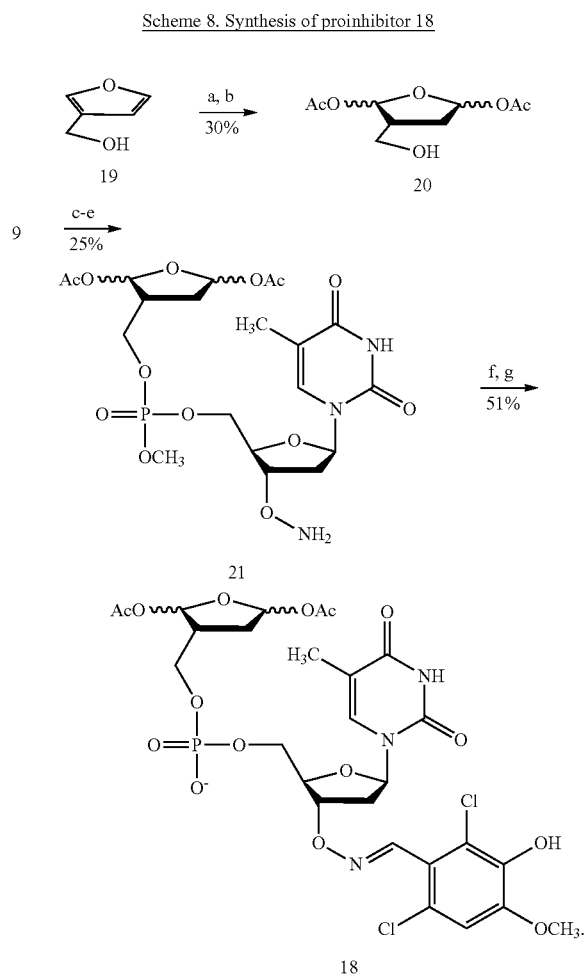

Key: a) Pb(OAc)$_4$
b) H$_2$/Rh
c) Phosphitylation
d) i. S-Ethyl-1H-tetrazole,20 ii.t-BuOOH
e) N$_2$H$_4$
f) 2,6-Dichloro-3-hydroxy-4-methoxybenzaldehyde, AcOH
g) Demethylation The ability of 18 to provide more effective inhibition than 3a directly was examined in prostate cancer cell (DU145) lysates. TLC analysis revealed that the bisacetate was converted to 3a within 5 min in DU145 lysate. The ability of 3a and 18 to inhibit DU 145 lysate lyase activity was then examined using 3'-$^{32}$P-15 as substrate (FIG. 11). Lyase activity inhibition was significantly greater by bisacetate 18 than 3a. Almost complete inhibition was achieved using 150 μM of 18, while more than 30% lyase activity remained following incubation with the same concentration of 3a. Varying the preincubation time of 18 with the cell lysate between 5 and 60 min showed that inactivation was complete by 15 min.

Example 8

Selective Targeting of Pol β in Cell Lysates

The selectivity of 3a for Pol β was examined further by incubating various cell lysates of mouse embryonic fibroblasts (MEFs) with proinhibitor 18 (Braithwaite et al., 2010). The lysates were obtained from cell lines that were established by breeding Pol β+/− and Pol λ+/− mice together. This yielded two wild type cell lines containing Pol β and Pol λ, as well as separate cell lines that either lack Pol β, Pol λ, or both. Cell lines that differ from wild type by the presence or absence of these polymerases are of interest because there is evidence that Pol λ acts as a back-up for Pol β during BER, although its lyase activity in vitro is considerably weaker than that of Pol β (Stevens et al., 2013; Braithwaite et al., 2010; Braithwaite et al., 2005). Consequently, it would be useful to know if 3a distinguished between the two enzymes. The 5'-deoxyribose phosphate lyase (dRPase) activity on 3'-$^{32}$P-15 of various MEF cell lysates was examined in the absence and presence of 18 (50 μM). Lyase reaction rates on 3'-$^{32}$P-15 were measured following preincubation of the lysate with 18 (or buffer). Preincubation with proinhibitor 18 reduced the rate of the lyase reaction almost 2-fold in lysates obtained from wild type cells (FIG. 12). The effect of 18 on lyase activity in cells lacking Pol λ (Pol λ-) was statistically indistinguishable (p=0.05) from reactivity in the wild type cells, suggesting that the inhibitor does not significantly inhibit this enzyme. The data presented in FIG. 12 are provided in Table 1, immediately herein below.

TABLE 1

Rate dependence of product formation on presence of inhibitor as a function of cell type.

| Cell Type | Inhibitor | Rate (×10$^{-1}$ % · min$^{-1}$)$^a$ | n$^b$ |
| --- | --- | --- | --- |
| Pol β wt | − | 17.2 ± 5.2 | 6 |
| Pol β wt | + | 9.2 ± 2.4 | 4 |
| Pol β - | − | 7.0 ± 2.1 | 6 |
| Pol β - | + | 5.5 ± 1.5 | 6 |
| Pol λ - | − | 15.9 ± 4.4 | 10 |
| Pol λ - | + | 9.1 ± 2.3 | 12 |
| Pol β/λ - | − | 15.0 ± 4.0 | 12 |
| Pol β/λ - | + | 11.0 ± 4.0 | 10 |
| Pol λ wt$^c$ | − | 23.7 ± 3.7 | 3 |
| Pot λ wt$^c$ | + | 12.4 ± 3.2 | 4 |

$^a$Reactions carried out in the presence of 32 μg protein. Aliquots taken at 5, 15, and 25 min. Rates are reported as the average ± std. dev. of n reactions.
$^b$Number of reactions used to determine average and standard deviation.
$^c$Aliquots taken at 2, 5, and 10 min.

The effect of 18 in lysates lacking Pol β was clearly different. The overall lyase activity in lysates lacking Pol β (in the absence of 18) was significantly lower than in those obtained from the wild type or Pol λ deficient cells, indicating that this enzyme was the major contributor to the lyase reaction with 3'-$^{32}$P-15. More importantly, 18 had a much smaller effect in Pol β-cells. The lyase activity was reduced less than 30% in the presence of 18 (FIG. 12). The effect of 18 on lyase activity in the double knock-out (Pol β-/Pol λ-) cells was within experimental error of that in the Pol β-cells, providing additional evidence that the inhibitor is selective for Pol β over Pol λ. However, the observation that 18 has even a small effect on the lyase reaction in the double knock-out or Pol β deficient cell lysates indicates that one or more other enzymes are affected by the proinhibitor.

Example 9

The Effects of 3a and 18 in Prostate Cancer Cells (DU145)

The superior performance of 18 compared to 3a in cell lysates was also evident in studies using DU145 cells. For instance, approximately 0.01% of the DU145 cells survived treatment with 40 μM 18, whereas 12% of the cells survived treatment with the same concentration of 3a (FIG. 13A). The above cell lysate experiments suggesting that the small molecule DOB mimics inhibit Pol β lyase activity, combined with the encouraging intracellular activity of 18 led to the examination of its ability to potentiate the cytotoxicity of a DNA damaging agent whose effects would require repair by Pol β. BER of DNA alkylated by methyl methanesulfonate (MMS) proceeds through an abasic site (AP, Scheme 1). Consequently, DU145 cell survival was measured as a function of MMS concentration, without and with 18 at a concentration (20 μM) where the proinhibitor itself results in approximately 45% cell death. After normalizing the fraction of surviving DU145 cells by taking into account the cytotoxicity of 18, plotting cell survival as a function of MMS concentration (FIG. 13B) reveals a clear potentiation (FIG. 13C) of the alkylating agent's cytotoxicity at 0.2 mM and above. The cytotoxicity of 18 (20 μM) and MMS (200 μM) is more than 2-fold greater than one would expect if the two agents were not acting synergistically. The synergistic effect of 18 and MMS is even greater at higher MMS concentrations but is difficult to quantify above 0.3 mM MMS where one observes a 5-fold potentiation, due to the small numbers of surviving cells. Interestingly, the level of potentiation observed by 18 is comparable and even slightly greater than that seen in cells in which either the Pol β gene is removed or its expression is knocked down using siRNA (Horton et al., 2003; Polosina et al., 2004).

Example 10

Conclusions

The kinetic experiments described above demonstrate that small molecules containing a 1,4-dicarbonyl, the same functional group present in DNA lesions that is responsible for inactivating Pol β (and Pol λ), irreversibly inhibit the lyase activity of this enzyme. These are believed to be the first suicide inhibitors that target the lyase activity of Pol β. Importantly, experiments in cell lysates derived from a variety of mouse embryonic fibroblasts lacking neither, one, or both Pol β or Pol λ, demonstrate that 18, which is enzymatically converted to 3a in lysates, selectively inhibits the lyase activity of the former over the latter. Although other enzymes that contribute to the lyase reaction of $^{32}$P-15 are affected more weakly by 18, overall the experiments involving mouse embryonic fibroblast lysates support inhibition of the targeted Pol β in cells. Pol λ is believed to back up BER by Pol β. Hence, developing molecules that selectively inhibit one of these enzymes over the other is useful for probing the enzymes' roles in DNA repair in cells (Strittmatter et al., 2013; Kuriyama et al., 2013). This suggests that 18 could be a useful tool for examining the effects of Pol β in cells. Furthermore, 18 functions as well or better than other molecules at potentiating the effects of a DNA damaging agent (MMS) in cells. This is believed to be the first example of an irreversible inhibitor of Pol β that works synergistically with and potentiates the cytotoxicity of a DNA damaging agent. There is a resurgence in interest in molecules that covalently modify their biological targets (Singh et al., 2011; Kwarcinski et al., 2012; Liu et al., 2013). The approach described here may be useful for inhibiting other DNA repair processes (Helleday et al., 2008).

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Albertella, M. R.; Lau, A.; O'Connor, M. J. DNA Repair 2005, 4, 583.

Barakat, K.; Gajewski, M.; Tuszynski, J. A. Curr. Top. Med. Chem. 2012, 12, 13761 390.

Boeckman, R. K.; Miller, J. R. Org. Lett. 2009, 11, 4544-4547.

Bournaud, C.; Marchal, E.; Quintard, A.; Sulzer-Mossé, S.; Alexakis, A. Tet. Asym. 2010, 21, 1666-1673.

Braithwaite, E. K.; Kedar, P. S.; Stumpo, D. J.; Bertocci, B.; Freedman, J. H.; Samson, L. D.; Wilson, S. H. PLoS One 2010, 5, e12229.

Braithwaite, E. K.; Prasad, R.; Shock, D. D.; Hou, E. W.; Beard, W. A.; Wilson, S. H. J. Biol. Chem. 2005, 280, 18469-18475.

Chen, F.; Gaucher, E. A.; Leal, N. A.; Flutter, D.; Havemann, S. A.; Govindarajan, S.; Ortlund, E. A.; Benner, S. A. Proc. Natl. Acad. Sci. USA 2010, 107, 1948-1953.

Chung, S.; Parker, J. B.; Bianchet, M.; Amzel, L. M.; Stivers, J. T. Nat. Chem. Biol. 2009, 5, 407-413.

Deterding, L. J.; Prasad, R.; Mullen, G. P.; Wilson, S. H.; Tomer, K. B. J. Biol. Chem. 2000, 275, 10463-10471.

Dianov, G. L.; Hübscher, U. Nucleic Acids Res. 2013, 41, 3483.

Donigan, K. A.; Hile, S. E.; Eckert, K. A.; Sweasy, J. B. DNA Repair 2012, 11, 381-390.

Donigan, K. A.; Sun, K.-w.; Nemec, A. A.; Murphy, D. L.; Cong, X.; Northrup, V.; Zelterman, D.; Sweasy, J. B. J. Biol. Chem. 2012, 287, 23830-23839.

Dorjsuren, D.; Wilson, D. M.; Beard, W. A.; McDonald, J. P.; Austin, C. P.; Woodgate, R.; Wilson, S. H.; Simeonov, A. Nucleic Acids Res. 2009, 37, e128-e128.

Feng, J.-A.; Crasto, C. J.; Matsumoto, Y. Biochemistry 1998, 37, 9605-9611.

Friedberg, E. C.; Walker, G., C.; Siede, W.; Wood, R. D.; Schultz, R. A.; Ellenberger, T. DNA Repair and Mutagenesis; 2nd ed.; ASM Press: Washington, D.C., 2006.

Gao, Z.; Maloney, D. J.; Dedkova, L. M.; Hecht, S. M. Bioorg. & Med. Chem. 2008, 16, 4331-4340.

Goldberg, I. H. Acc. Chem. Res. 1991, 24, 191-198.

Guan, L.; Bebenek, K.; Kunkel, T. A.; Greenberg, M. M. Biochemistry 2010, 49, 9904-9910.

Guan, L.; Greenberg, M. M. J. Am. Chem. Soc. 2010, 132, 5004-5005.

Helleday, T.; Petermann, E.; Lundin, C.; Hodgson, B.; Sharma, R. A. Nat. Rev. Cancer 2008, 8, 193-204.

Horton, J. K.; Joyce-Gray, D. F.; Pachkowski, B. F.; Swenberg, J. A.; Wilson, S. H. DNA Repair 2003, 2, 27-48.

Horton, J. K.; Watson, M.; Stefanick, D. F.; Shaughnessy, D. T.; Taylor, J. A.; Wilson, S. H. Cell Res. 2008, 18, 48-63.

Husain, I.; Arteaga, C. L.; Srivastava, D. K.; Wilson, S. H. Carcinogenesis 1999, 20, 1049-1054.

Jacobs, A. C.; Kreller, C. R.; Greenberg, M. M. Biochemistry 2011, 50, 136-143.

Jessen, H. J.; Schulz, T.; Balzarini, J.; Meier, C. Angew. Chem. Int. Ed. 2008, 47, 8719-8722.

Jiang, Y. L.; Krosky, D. J.; Seiple, L.; Stivers, J. T. J. Am. Chem. Soc. 2005, 127, 17412-17420.

Kodama, T.; Greenberg, M. M. J. Org. Chem. 2005, 70, 9916-9924.

Kuriyama, I.; Miyazaki, A.; Tsuda, Y.; Yoshida, H.; Mizushina, Y. Bioorg. & Med. Chem. 2013, 21, 403-411.

Kwarcinski, F. E.; Fox, C. C.; Steffey, M. E.; Soellner, M. B. ACS Chemical Biology 2012, 7, 1910-1917.

Lindahl, T. in Progress in Nucleic Acid Research and Molecular Biology, Vol. 68 (Ed.: K. Moldave), Academic Press, San Diego, 2001, pp. xvii.

Liu, Q.; Sabnis, Y.; Zhao, Z.; Zhang, T.; Buhrlage, S. J.; Jones, L. H.; Gray, N. S. Chemistry & Biology 2013, 20, 146-159.

Liu, J.; Wong, C.-H. Tetrahedron Lett. 2002, 43, 4037-4039.

Matsumoto, Y.; Kim, K. Science 1995, 269, 699-702.

Matsumoto, Y.; Kim, K.; Katz, D. S.; Feng, J.-A. Biochemistry 1998, 37, 6456-6464.

Mootoo, D. R.; Date, V.; Fraser-Reid, B. J. Am. Chem. Soc. 1988, 110, 2662-2663.

Nakamura, R.; Takeuchi, R.; Kuramochi, K.; Mizushina, Y.; Ishimaru, C.; Takakusagi, Y.; Takemura, M.; Kobayashi, S.; Yoshida, H.; Sugawara, F.; Sakaguchi, K. Org. & Biomol. Chem. 2007, 5, 3912-3921.

Nemec, A. A.; Donigan, K. A.; Murphy, D. L.; Jaeger, J.; Sweasy, J. B. J. Biol. Chem. 2012, 287, 23840-23849.

Ora, M.; Taherpour, S.; Linna, R.; Leisvuori, A.; Hietamaki, E.; Poijarvi-Virta, P.; Beigelman, L.; Lönnberg, H. J. Org. Chem. 2009, 74, 4992-5001.

Pascucci, B.; Maga, G.; Habscher, U.; Bjoras, M.; Seeberg, E.; Hickson, I. D.; Villani, G.; Giordano, C.; Cellai, L.; Dogliotti, E. Nucleic Acids Res. 2002, 30, 2124.

Pitié, M.; Pratviel, G. Chem. Rev. 2010, 110, 1018-1059.

Polosina, Y. Y.; Rosenquist, T. A.; Grollman, A. P.; Miller, H. DNA Repair 2004, 3, 1469-1474.

Prasad, R.; Batra, V. K.; Yang, X. P.; Krahn, J. M.; Pedersen, L. C.; Beard, W. A.; Wilson, S. H. DNA Repair 2005, 4, 1347-1357.

Prasad, R.; Beard, W. A.; Chyan, J. Y.; Maciejewski, M. W.; Mullen, G. P.; Wilson, S. H. J. Biol. Chem. 1998, 273, 11121-11126.

Prasad, R.; Beard, W. A.; Strauss, P. S.; Wilson, S. H. J. Biol. Chem. 1998, 273, 15263-15270.

Silverman, R. B. The Organic Chemistry of Enzyme-Catalyzed Reactions; Academic Press: San Diego, 2000.

Singh, J.; Petter, R. C.; Baillie, T. A.; Whiny, A. Nat. Rev. Drug Discov. 2011, 10, 307-317.

Sobol, R. W.; Horton, J. K.; Kuhn, R.; Gu, H.; Singhal, R. K.; Prasad, R.; Rajewsky, K.; Wilson, S. H. Nature 1996, 379, 183.

Sobol, R. W.; Prasad, R.; Evenski, A.; Baker, A.; Yang, X. P.; Horton, J. K.; Wilson, S. H. Nature 2000, 405, 807.

Starcevic, D.; Dalal, S.; Sweasy, J. B. Cell Cycle 2004, 3, 998-1001.

Stevens, A. J.; Guan, L.; Bebenek, K.; Kunkel, T. A.; Greenberg, M. M. Biochemistry 2013, 52, 975-983.

Stivers, J. T.; Jiang, Y. L. Chem. Rev. 2003, 103, 2729-2759.

Strittmatter, T.; Bareth, B.; Immel, T. A.; Huhn, T.; Mayer, T. U.; Marx, A. ACS Chem. Biol. 2011, 6, 314-319.

Strittmatter, T.; Brockmann, A.; Pott, M.; Hantusch, A.; Brunner, T.; Marx, A. ACS Chem. Biol. 2013, doi: 10.1021/cb4007562.

Wilson, S. H.; Beard, W. A.; Shock, D. D.; Batra, V. K.; Cavanaugh, N. A.; Prasad, R.; Hou, E. W.; Liu, Y. A.; Asagoshi, K.; Horton, J. K.; Stefanick, D. F.; Kedar, P. S.; Carrozza, M. J.; Masaoka, A.; Heacock, M. L. Cell. Mol. Life. Sci. 2010, 67, 3633-3647.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A compound of formula (I):

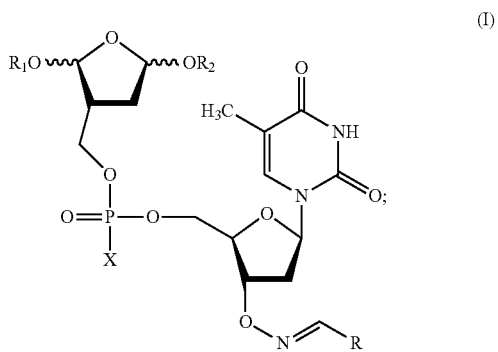

wherein:

X is selected from the group consisting of alkyl, alkoxyl, O⁻, and S⁻;

R is selected from the group consisting of substituted or unsubstituted alkyl, heteroalkyl, cycloalkyl, cycloalkylalkyl, cycloheteroalkyl, aryl, heteroaryl, arylalkyl, heteroarylalkyl, multicyclic aliphatic ring systems, multicylic aromatic ring systems, fused aliphatic ring systems, fused aromatic ring systems, and combinations thereof;

$R_1$ and $R_2$ are each independently selected from the group consisting of hydrogen and —(=O)-alkyl; and pharmaceutically acceptable salts thereof.

2. The compound of claim 1, wherein R is selected from the group consisting of a substituent group provided in FIG. 1.

3. The compound of claim 1, wherein the compound of formula (I) is selected from the group consisting of:

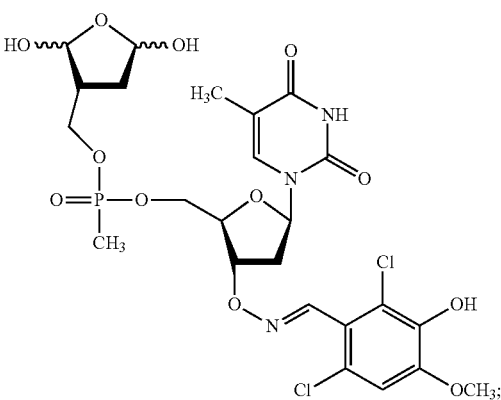

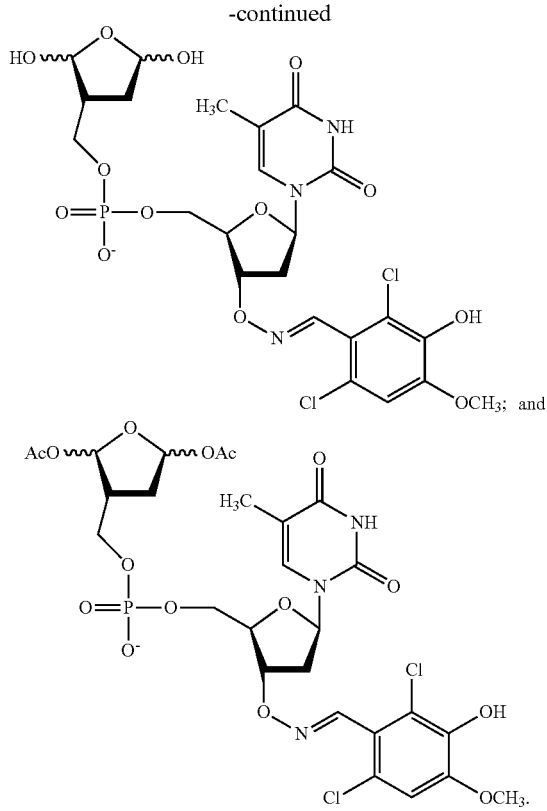

4. A method for irreversibly inhibiting a DNA repair enzyme that possesses lyase activity in a subject, the method comprising administering to the subject a therapeutically effective amount of a compound of Formula (I):

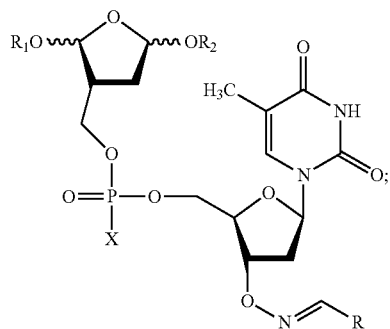

wherein:
X is selected from the group consisting of alkyl, alkoxyl, O⁻, and S⁻;
R is selected from the group consisting of substituted or unsubstituted alkyl, heteroalkyl, cycloalkyl, cycloalkylalkyl, cycloheteroalkyl, aryl, heteroaryl, arylalkyl, heteroarylalkyl, multicyclic aliphatic ring systems, multicylic aromatic ring systems, fused aliphatic ring systems, fused aromatic ring systems, and combinations thereof.
$R_1$ and $R_2$ are each independently selected from the group consisting of hydrogen and —(═O)-alkyl; and pharmaceutically acceptable salts thereof.

5. The method of claim 4, wherein R is selected from the group consisting of a substituent group provided in FIG. 1.

6. The method of claim 4, wherein the compound of formula (I) is selected from the group consisting of:

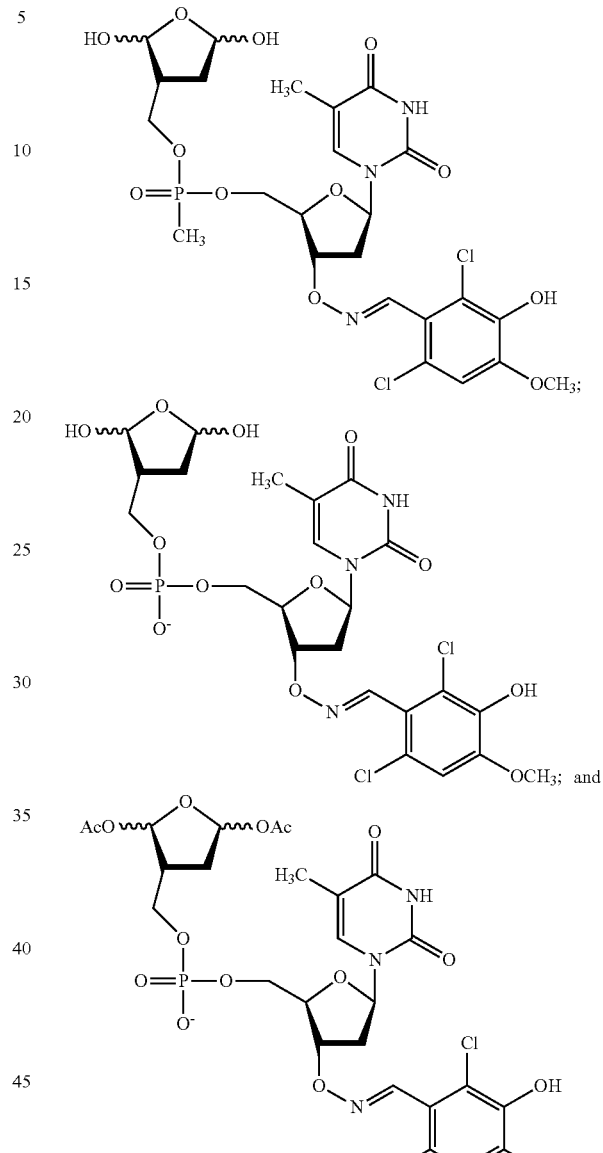

7. The method of claim 4, wherein the DNA repair enzyme is selected from the group consisting of DNA polymerase β, 5'-deoxyribose-5-phosphate lyase Ku70, and Endonuclease III-like protein 1.

8. The method of claim 4, wherein the compound inhibits the lyase activity of the DNA repair enzyme.

9. The method of claim 4, wherein the subject has cancer.

10. The method of claim 8, wherein inhibiting the DNA repair enzyme treats, inhibits, delays, or prevents the spread of the cancer in the subject.

11. The method of claim 10, further comprising treating, inhibiting, delaying, or preventing the spread of the cancer by inhibiting at least one cancer cell involved in one or more biological processes selected from the group consisting of cell migration, cell growth, cell adhesion, angiogenesis, cancer cell invasion, apoptosis, tumor formation, tumor progression, metastasis, degradation of the extracellular matrix, pericellular proteolysis, activation of plasminogen, and changes in the levels of an extracellular protease.

12. The method of claim 4, further comprising administering to the subject a DNA damaging agent.

13. The method of claim 12, wherein the DNA damaging agent is methyl methanesulfonate (MMS).

14. The method of claim 12, wherein the DNA damaging agent is administered before, simultaneously, or after administration of the compound of Formula (I).

15. A method for inhibiting a cancer cell, the method comprising contacting the cancer or noncancerous cell with a compound of Formulae (I) in an amount effective to irreversibly inhibit a DNA repair enzyme that possesses lyase activity:

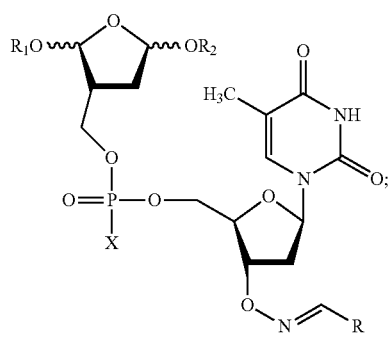

(I)

wherein:
X is selected from the group consisting of alkyl, alkoxyl, O$^-$, and S$^-$;
R is selected from the group consisting of substituted or unsubstituted alkyl, heteroalkyl, cycloalkyl, cycloalkylalkyl, cycloheteroalkyl, aryl, heteroaryl, arylalkyl, heteroarylalkyl, multicyclic aliphatic ring systems, multicylic aromatic ring systems, fused aliphatic ring systems, fused aromatic ring systems, and combinations thereof.
R$_1$ and R$_2$ are each independently selected from the group consisting of hydrogen and —(=O)-alkyl; and
pharmaceutically acceptable salts thereof.

16. A method for irreversibly inhibiting a DNA repair enzyme that possesses lyase activity, the method comprising contacting the DNA repair enzyme with a compound of Formula (I) wherein contacting the DNA repair enzyme with the compound irreversibly inhibits the DNA repair enzyme:

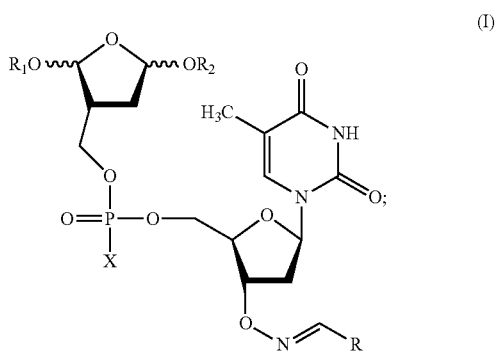

(I)

wherein:
X is selected from the group consisting of alkyl, alkoxyl, O$^-$, and S$^-$;
R is selected from the group consisting of substituted or unsubstituted alkyl, heteroalkyl, cycloalkyl, cycloalkylalkyl, cycloheteroalkyl, aryl, heteroaryl, arylalkyl, heteroarylalkyl, multicyclic aliphatic ring systems, multicylic aromatic ring systems, fused aliphatic ring systems, fused aromatic ring systems, and combinations thereof.
R$_1$ and R$_2$ are each independently selected from the group consisting of hydrogen and —(=O)-alkyl; and
pharmaceutically acceptable salts thereof.

17. The method of claim 16, wherein the DNA repair enzyme is selected from the group consisting of DNA polymerase β, 5'-deoxyribose-5-phosphate lyase Ku70, and Endonuclease III-like protein 1.

18. The method of claim 16, wherein the compound inhibits the lyase activity of the DNA repair enzyme.

19. The method of claim 16, further comprising contacting the DNA repair enzyme with a DNA damaging agent.

20. The method of claim 19, wherein the DNA damaging agent is methyl methanesulfonate (MMS).

21. The method of claim 16, wherein inhibiting the DNA repair enzyme occurs in vitro, in vivo, or ex vivo.

* * * * *